United States Patent
Belhadj-Tahar et al.

(10) Patent No.: US 9,603,953 B2
(45) Date of Patent: Mar. 28, 2017

(54) DENDRIMER COMPOSITIONS, METHODS OF SYNTHESIS, AND USES THEREOF

(71) Applicants: Guanghua Yang, L'Isle Adam (FR); Hafid Belhadj-Tahar, Toulouse (FR); Nouredine Sadeg, Osny (FR)

(72) Inventors: Hafid Belhadj-Tahar, Toulouse (FR); Nouredine Sadeg, Osny (FR); Yvon Coulais, Clermont-Pouyguilles (FR)

(73) Assignees: Guanghua Yang (FR); Hafid Belhadj-Tahar (FR); Nouredine Sadeq (FR)

( * ) Notice: Subject to any disclaimer, the term of this patent is extended or adjusted under 35 U.S.C. 154(b) by 0 days.

(21) Appl. No.: 14/902,208

(22) PCT Filed: Jan. 13, 2014

(86) PCT No.: PCT/IB2014/058238
§ 371 (c)(1),
(2) Date: Dec. 30, 2015

(87) PCT Pub. No.: WO2015/104589
PCT Pub. Date: Jul. 16, 2015

(65) Prior Publication Data
US 2016/0303261 A1    Oct. 20, 2016

(51) Int. Cl.
| | |
|---|---|
| A61K 51/00 | (2006.01) |
| A61M 36/14 | (2006.01) |
| A61K 51/08 | (2006.01) |
| A61K 45/06 | (2006.01) |
| A61K 47/48 | (2006.01) |
| C08G 69/48 | (2006.01) |
| A61K 51/06 | (2006.01) |

(52) U.S. Cl.
CPC ............ *A61K 51/088* (2013.01); *A61K 45/06* (2013.01); *A61K 47/48246* (2013.01); *C08G 69/48* (2013.01); *A61K 51/06* (2013.01)

(58) Field of Classification Search
CPC ..................................................... A61K 51/06
See application file for complete search history.

(56) References Cited

U.S. PATENT DOCUMENTS

| | | |
|---|---|---|
| 4,507,466 A | 3/1985 | Tomalia et al. |
| 4,558,120 A | 12/1985 | Tomalia et al. |
| 4,568,737 A | 2/1986 | Tomalia et al. |
| 4,587,329 A | 5/1986 | Tomalia et al. |
| 4,631,337 A | 12/1986 | Tomalia et al. |
| 4,694,064 A | 9/1987 | Tomalia et al. |
| 4,713,975 A | 12/1987 | Tomalia et al. |
| 4,737,550 A | 4/1988 | Tomalia |
| 4,857,599 A | 8/1989 | Tomalia et al. |
| 4,871,779 A | 10/1989 | Killat et al. |
| 5,338,532 A | 8/1994 | Tomalia et al. |
| 5,354,308 A | 10/1994 | Simon et al. |
| 5,387,617 A | 2/1995 | Hedstrand et al. |
| 5,393,795 A | 2/1995 | Hedstrand et al. |
| 5,393,797 A | 2/1995 | Hedstrand et al. |
| 5,527,524 A | 6/1996 | Tomalia et al. |
| 5,560,929 A | 10/1996 | Hedstrand et al. |
| 5,631,329 A | 5/1997 | Yin et al. |
| 5,674,192 A | 10/1997 | Sahatjian et al. |
| 5,674,693 A | 10/1997 | Raleigh et al. |
| 5,693,014 A | 12/1997 | Abele et al. |
| 5,733,303 A | 3/1998 | Israel et al. |
| 5,755,722 A | 5/1998 | Barry et al. |
| 5,773,527 A | 6/1998 | Tomalia et al. |
| 5,792,105 A | 8/1998 | Lin et al. |
| 5,800,391 A | 9/1998 | Kontos |
| 5,800,508 A | 9/1998 | Goicoechea et al. |
| 5,800,519 A | 9/1998 | Sandock |
| 5,843,089 A | 12/1998 | Sahatjian et al. |
| 5,851,228 A | 12/1998 | Pinheiro |
| 5,857,998 A | 1/1999 | Barry |
| 5,866,561 A | 2/1999 | Ungs |
| 5,868,719 A | 2/1999 | Tsukernik |
| 5,876,445 A | 3/1999 | Andersen et al. |
| 5,908,413 A | 6/1999 | Lang et al. |
| 5,913,894 A | 6/1999 | Schmitt |
| 5,933,145 A | 8/1999 | Meek |
| 5,935,114 A | 8/1999 | Jang et al. |
| 6,471,968 B1 | 10/2002 | Baker, Jr. et al. |
| 2011/0002850 A1 | 1/2011 | Collier et al. |

FOREIGN PATENT DOCUMENTS

EP     2906613 B1    3/2016

OTHER PUBLICATIONS

B M Seddon et al. "The role of functional and molecular imaging in cancer drug discovery and development" The British Journal of Radiology, 2003, vol. 76, pp. S128-S138.
David M. Brizel et al. "Tumor Oxygenation Predicts for the Likelihood of Distant Metastases in Human Soft Tissue Sarcoma", Advance in Brief Cancer Research, Mar. 1, 1996, vol. 56, pp. 941-943.
Eric Benoist et al. "A Click procedure with heterogeneous copper to tether technetium-99m chelating agents and rhenium complexes. Evaluation of the chelating properties and biodistribution of the new radiolabelled glucose conjugates", Carbohydrate Research ,, 2011, vol. 346, pp. 26-34.
G.E. Adams "Hypoxia-Mediated Drugs for Radiation and Chemotherapy", American Cancer Society, 1981, vol. 48, No. 3, pp. 696-707.
H. Belhadj-Tahar et al., "Etudes de Toxicocinetique et de biodistribution de dendrimeres de cinquieme generation", 8emes Journees Cancerop6le Grand Sud Ouest Oct. 10-12, 2012, MontpelierLett., 9 (2007), pp. 4999-5002.

(Continued)

*Primary Examiner* — Frederick Krass
*Assistant Examiner* — Melissa Perreira
(74) *Attorney, Agent, or Firm* — Cantor Colburn LLP

(57) ABSTRACT

The disclosure relates to novel dendrimer conjugates and the methods of synthesizing the same, as well as systems and methods utilizing the dendrimer conjugates (e.g., in diagnostic and/or therapeutic settings (e.g., for the delivery of therapeutics, imaging, and/or targeting agents (e.g., in disease diagnosis and/or therapy, etc.))).

21 Claims, 7 Drawing Sheets

(56) References Cited

OTHER PUBLICATIONS

Hafid Belhadj-Tahar et al. "Conceptualization and assessment of original probes for hypoxic cell exploration", 2nd Symposium Novel Targeting drugs and radiotherapy, Jun. 14-15, 2007, Toulouse France.
Holger Palmedo et al. "Dose escalation study with rhenium-188 hydroxyetheylidene diphosphonate in prostate cancer patients with osseous metastases", European Journal of Nuclear Medicine, Feb. 2000, vol. 27, No. 2, pp. 123-130.
Jurgen Grunberg et al. "DOTA-Functionalized Polylysine: A High Number of DOTA Chelates Positively Influences the Biodistribution of Enzymatic Conjugated Anti-Tumor Antibody chCE7agl", PLOS One, Apr. 2013, vol. 8, No. 4, pp. 1-10.
Lisa M. Kaminskas et al. "Phamacokinetics and Tumor Disposition of PEGylated Methotrexate Cunjudated Poly-L-lysine Dendrimer" Molecular Pharmaceutics, 2009, vol. 6, No. 3, pp. 1190-1204.
Manfred Kunz et al. "Molecular responses to hypoxia in tumor cells", Molecular Cancer Apr. 17, 2003, vol. 2, pp. 1-13.
Nathalie Launay et al. "A General Synthetic Strategy for Neutral Phosphorus-Containing Dendrimers", Angewandte Chemie International Edition in English, 1994, vol. 33, No. 15/16, pp. 1589-1592.
Nathalie Launay et al. "Synthesis of bowl-shaped dendrimers from generation 1 to generation 8", Journal of Organometallic Chemistry, 1997, vol. 529, pp. 51-58.
Riad Salem et al. "Radioembolization for Hepatocellular Carcinoma Using Yttrium-90 Miscrospheres: A Comprehensive Report of Long-term Outcomes", www.gastro.org/gastropodcast, 2010, vol. 138, No. 1, pp. 52-54.
Richard Rupp et al. "VivaGel (SPL7013 Gel):A candidate dendrimer-microbicide for the prevention of HIV and HSV infection", International Journal of Nanomedicine, 2007, vol. 2, No. 4, pp. 561-566.

Typical dendrimer structure starting from a core with three functional groups.

| | % Injected dose / Organ ||||||||| 
|---|---|---|---|---|---|---|---|---|---|
| | G5 ||| G5-HLS ||| HLS |||
| | mean | Standard deviation | C.V. % | mean | Standard deviation | C.V. % | mean | Standard deviation | C.V. % |
| Carcass | 11,80% | 12,04% | 102,0% | 15,72% | 3,21% | 20,4% | 32,68% | 3,16% | 9,7% |
| Liver | 15,71% | 26,14% | 166,3% | 16,44% | 11,16% | 67,9% | 18,18% | 9,32% | 51,3% |
| Small intestin | 2,53% | 2,24% | 88,6% | 46,72% | 24,02% | 51,4% | 21,94% | 15,91% | 72,5% |
| Colon | 25,91% | 44,29% | 171,0% | 1,06% | 0,48% | 44,8% | 1,50% | 0,22% | 14,4% |
| Stomach | 2,66% | 2,35% | 88,2% | 6,39% | 3,66% | 57,3% | 15,22% | 1,26% | 8,3% |
| Pancreas | 1,51% | 2,53% | 167,4% | 1,61% | 1,20% | 74,6% | 1,96% | 1,62% | 82,6% |
| Heart | 0,13% | 0,19% | 150,5% | 0,12% | 0,10% | 81,4% | 0,13% | 0,05% | 39,6% |
| Lungs | 1,72% | 2,91% | 169,1% | 0,90% | 1,22% | 135,1% | 1,00% | 1,09% | 108,2% |
| Kidneys | 1,39% | 2,12% | 152,0% | 1,46% | 0,74% | 51,0% | 1,43% | 0,88% | 61,5% |
| Spleen | 0,82% | 1,35% | 163,9% | 0,92% | 1,44% | 157,3% | 0,90% | 1,38% | 153,7% |
| Testicles | 0,00% | 0,00% | 93,0% | 0,00% | 0,00% | 11,0% | 0,00% | 0,00% | 23,4% |
| Brain | 0,01% | 0,01% | 103,9% | 0,01% | 0,01% | 40,0% | 0,00% | 0,00% | 172,9% |
| Blood | 2,24% | 2,34% | 104,2% | 2,69% | 0,82% | 30,5% | 7,10% | 0,85% | 11,9% |
| Urine | 0,33% | 0,58% | 173,2% | 0,00% | 0,00% | 11,0% | 1,61% | 1,57% | 97,6% |

FIGURE 2

| | % Injected dose / g Organ | | | | | | | | |
|---|---|---|---|---|---|---|---|---|---|
| | G5 | | | G5-HLS | | | HLS | | |
| | mean | Standard deviation | C.V. % | mean | Standard deviation | C.V. % | mean | Standard deviation | C.V. % |
| Carcass | 0,05% | 0,05% | 105,2% | 0,07% | 0,01% | 20,0% | 0,10% | 0,01% | 9,8% |
| Liver | 1,46% | 2,44% | 166,9% | 1,53% | 1,07% | 69,6% | 1,59% | 0,88% | 55,4% |
| Small intestin | 0,20% | 0,18% | 86,6% | 3,59% | 1,93% | 53,8% | 1,61% | 1,24% | 77,3% |
| Colon | 3,01% | 5,13% | 170,3% | 0,16% | 0,07% | 44,8% | 0,18% | 0,03% | 16,2% |
| Stomach | 0,46% | 0,44% | 96,1% | 1,29% | 0,87% | 67,0% | 2,06% | 0,44% | 21,1% |
| Pancreas | 1,61% | 2,69% | 166,7% | 1,46% | 1,03% | 70,2% | 1,67% | 1,07% | 64,3% |
| Heart | 0,12% | 0,17% | 148,3% | 0,12% | 0,09% | 79,5% | 0,12% | 0,05% | 40,1% |
| Lungs | 1,16% | 1,93% | 166,6% | 0,58% | 0,75% | 128,3% | 0,57% | 0,64% | 112,1% |
| Kidneys | 0,59% | 0,88% | 148,4% | 0,68% | 0,28% | 41,4% | 0,63% | 0,38% | 60,8% |
| Spleen | 1,06% | 1,73% | 163,3% | 0,85% | 1,32% | 155,0% | 1,05% | 1,60% | 152,8% |
| Testicles | 0,00% | 0,00% | 93,0% | 0,00% | 0,00% | 11,0% | 0,00% | 0,00% | 23,4% |
| Brain | 0,01% | 0,01% | 101,2% | 0,01% | 0,00% | 42,1% | 0,00% | 0,00% | 137,2% |
| Blood | 0,11% | 0,12% | 107,5% | 0,13% | 0,04% | 28,4% | 0,27% | 0,03% | 10,7% |
| Urine | 0,35% | 0,60% | 173,1% | 0,00% | 0,00% | 67,2% | 1,88% | 1,64% | 87,2% |

FIGURE 3

DENDRIMER COMPOSITIONS, METHODS OF SYNTHESIS, AND USES THEREOF

BACKGROUND OF THE INVENTION

Dendrimers are macromolecules consisting of monomers which are associated according to a tree-structured process around a multifunctional central core.

Dendrimers, also called "cascade molecules", are highly branched functional polymers with a defined structure. These macromolecules are actually polymers since they are based on the association of recurrent units. However, dendrimers fundamentally differ from conventional polymers insofar that they have specific properties due to their tree-structured construction. The molecular weight and the shape of the dendrimers may be accurately controlled and the functions are located at the ending of the tree-structures, forming a surface, which makes them easily accessible.

Dendrimers are built step by step, by repeating a sequence of reactions allowing the multiplication of each recurrent unit and of the terminal functions. Each sequence of reactions forms what is called a "new generation". The tree-structured construction is carried out by repeating a sequence of reactions with which a new generation and an increasing number of identical branches may be obtained at the end of each reaction cycle. After a few generations, the dendrimer assumes a highly branched and multifunctionalized globular shape by the numerous terminal functions present at the periphery.

Such polymers were notably described by Launay et al., Angew. Chem. Int. Ed. Engl., 1994, 33, 15/16, 1590-1592, [1] or further Launay et al., Journal of Organometallic Chemistry, 1997, 529, 51-58. [2]

Hypoxic tumors are clinically very difficult to treat: they are resistant to radiation and chemotherapy treatments and are often accrue treatments [3]

However, hypoxic tumor cells are known to be very aggressive and spread rapidly as metastasis throughout the body.[4]

Because hypoxic tumors respond poorly to conventional treatments (radiation and chemotherapy), other therapeutic options have emerged as hyperbaric oxygen, and sensitiving agents by bioreducing action.[5]

In this example, bioreducing agents like family of nitro-imidazole, are reduced by hypoxic tumor cells by intracellular metabolites leading to form anionic radicals which react intracellularly.

Before this "homeless therapeutic" new methods of intra-arterial administration of cytotoxic agents (radiotherapy=yttrium radiation, chemotherapy=doxorubicin and some chemical congeners) have greatly improved the prognosis. [6]

In situ cancer therapy is the solution of choice in the recurrence and metastasis beyond the systemic therapy and for reasons related to resistance or exceeded the tolerated dose for antimitotic used in previous treatments.

In situ radiotherapy by intra arteriography administration is proposed for the treatment of metastases resistant large in relation to their hypoxic state. But so far, this technique uses a non-diffusible generally formed of adsorbed yttrium-90 microspheres.

In the absence of intratumoral diffusion and non-specificity of the product used, this treatment is based solely on the physical path of ionizing radiation, has a very limited effectiveness in the presence of a large tumor.

Accordingly, there is a great need to develop new compounds useful for treatment of cancer, in particular, compounds that may help improve the prognosis of these patients who are currently considered palliative.

BRIEF DESCRIPTION OF THE DRAWING

FIG. 2 shows a table compiling a statistical summary of the biodistribution results of Example 5 in terms of % injected dose/organ (% Injected dose/Organ=100%×(Dose fixed by organ/Total dose injected initially)).

FIG. 3 shows a table compiling a statistical summary of the biodistribution results of Example 5 in terms of % injected dose/g organ (% Injected dose/g organ=[100%×(Dose fixed by organ/Total dose injected initially)]/weight of organ).

DEFINITIONS

Figure 1:
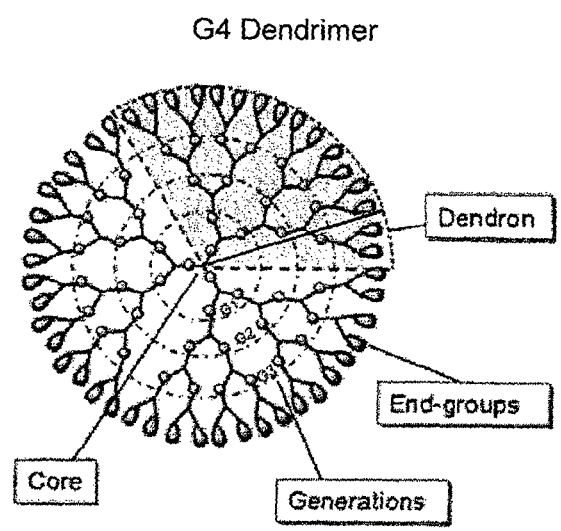
FIG. 1 shows a typical dendrimer structure that has a core with three functional groups.
Figure 4:
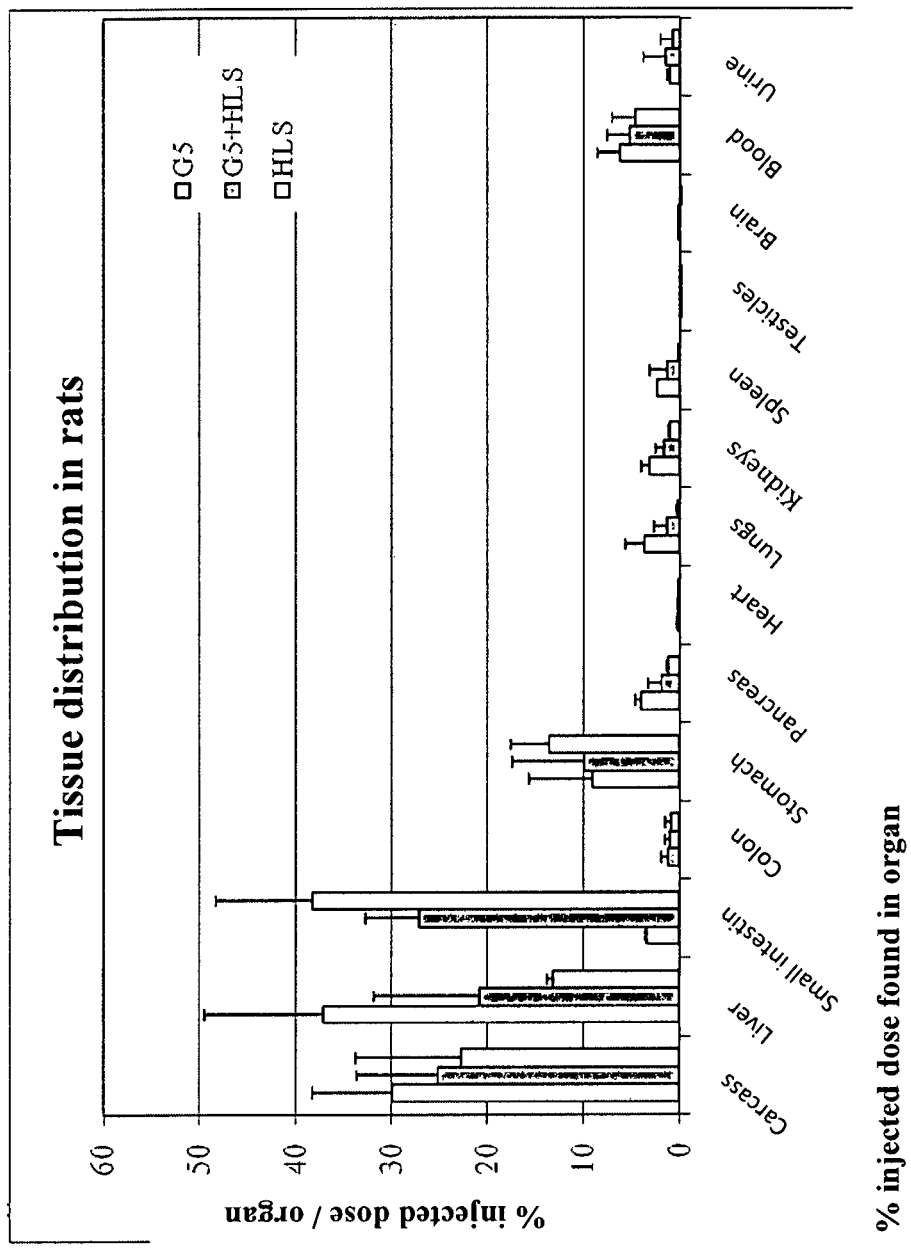
FIGS. 4 and 5 depict the results of FIGS. 2 and 3, in graphic form, respectively.
Figure 5:
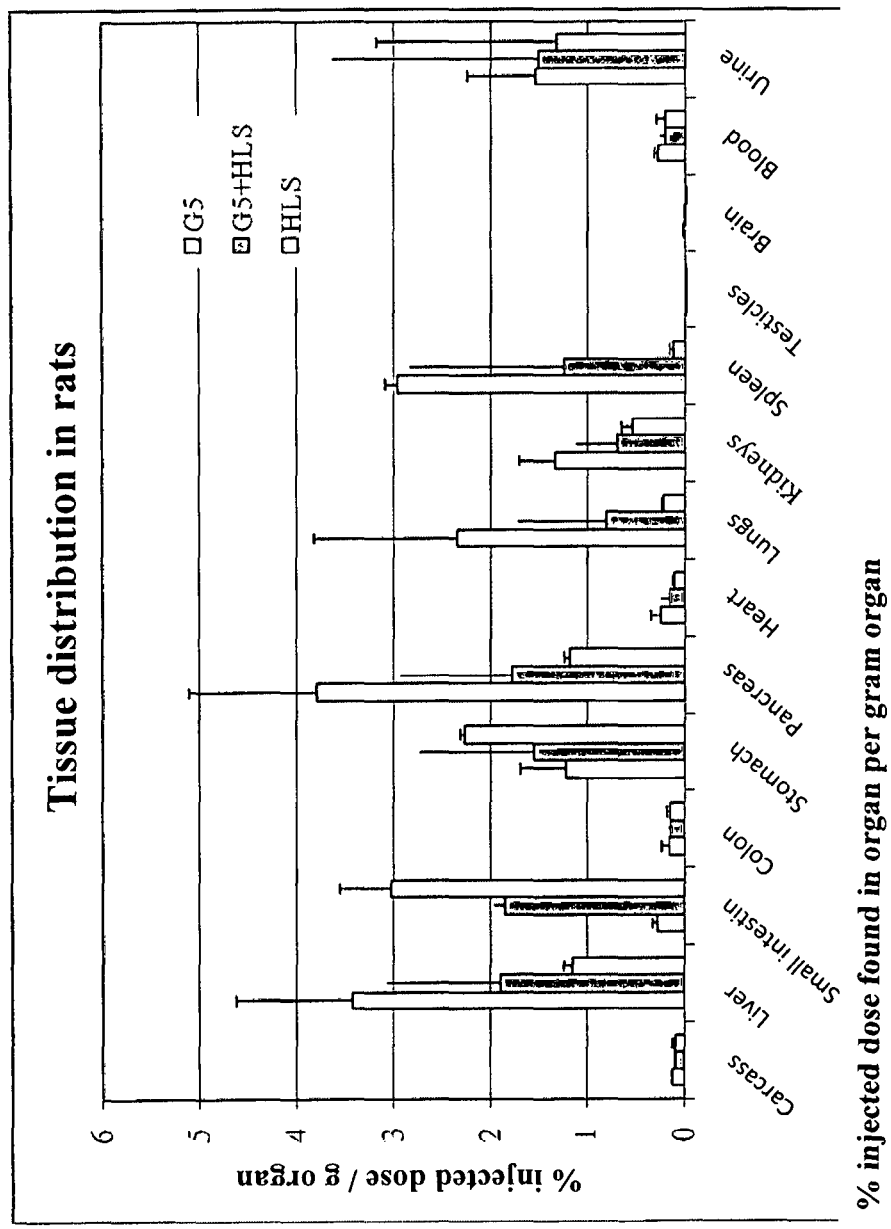

To facilitate an understanding of the present invention, a number of terms and phrases are defined below:

As used herein, the term "subject" refers to any animal (e.g., a mammal), including, but not limited to, humans, non-human primates, rodents, and the like, which is to be the recipient of a particular treatment. Typically, the terms "subject" and "patient" are used interchangeably herein in reference to a human subject. As used herein, the term "subject" may encompass subjects suspected of having cancer, subjects diagnosed with a cancer, and/or subjects at risk for cancer.

As used herein, the term "subject suspected of having cancer" refers to a subject that presents one or more symptoms indicative of a cancer (e.g., a noticeable lump or mass) or is being screened for a cancer (e.g., during a routine physical). A subject suspected of having cancer may also have one or more risk factors. A subject suspected of having cancer has generally not been tested for cancer. However, a "subject suspected of having cancer" encompasses an individual who has received a preliminary diagnosis (e.g., a CT scan showing a mass) but for whom a confirmatory test (e.g., biopsy and/or histology) has not been done or for whom the stage of cancer is not known. The term further includes people who once had cancer (e.g., an individual in remission). A "subject suspected of having cancer" is sometimes diagnosed with cancer and is sometimes found to not have cancer.

As used herein, the term "subject diagnosed with a cancer" refers to a subject who has been tested and found to have cancerous cells. The cancer may be diagnosed using any suitable method, including but not limited to, biopsy, x-ray, blood test, and the diagnostic methods of the present invention.

As used herein, the term "subject at risk for cancer" refers to a subject with one or more risk factors for developing a specific cancer. Risk factors include, but are not limited to, gender, age, genetic predisposition, environmental expose, and previous incidents of cancer, preexisting non-cancer diseases, and lifestyle.

As used herein, the term "stage of cancer" refers to a qualitative or quantitative assessment of the level of advancement of a cancer. Criteria used to determine the stage of a cancer include, but are not limited to, the size of the tumor, whether the tumor has spread to other parts of the body and where the cancer has spread (e.g., within the same organ or region of the body or to another organ).

As used herein, the term "improving a prognosis" refers to lessening the impact of the presence of cancer (e.g., as determined by the diagnostic methods of the present invention) on a subject's future health (e.g., expected morbidity or mortality, the likelihood of getting cancer, and the risk of metastasis). As used herein, the term "non-human animals" refers to all non-human animals including, but not limited to, vertebrates such as rodents, non-human primates, ovines, bovines, ruminants, lagomorphs, porcines, caprines, equines, canines, felines, ayes, etc.

The term "treating", as used herein generally means that the compounds of the invention can be used in humans or animals with at least a tentative diagnosis of disease. In certain embodiments, compounds of the invention will delay or slow the progression of the disease thereby giving the individual a longer life span.

The term "preventing" as used herein means that the compounds of the present invention are useful when administered to a patient who has not been diagnosed as possibly having the disease at the time of administration, but who would normally be expected to develop the disease or be at increased risk for the disease. The compounds of the invention will slow the development of disease symptoms, delay the onset of disease, or prevent the individual from developing the disease at all. Preventing also includes administration of the compounds of the invention to those individuals thought to be predisposed to the disease due to familial history, genetic or chromosomal abnormalities, and/or due to the presence of one or more biological markers for the disease.

DETAILED DESCRIPTION OF CERTAIN PREFERRED EMBODIMENTS OF THE INVENTION

As noted above, there has been increasing interest in recent years in the development of new compounds useful for treatment of cancer, in particular, compounds that may help improve the prognosis of these patients who are currently considered palliative.

In this context, there is provided herein the use of dendrimers as supravector emitters targeting hypoxic cells. For example they can be supravector emitters in β complexes of rhenium-186.

In one advantageous aspect, the invention combines:

Firstly, a spherical supramolecular dendrimer vector whose diameter is adaptable to embolize neovascularization of tumor stroma. When embolization of tumor neovascularizations; radio-complexes diffuse freely in space of the tumor and will preferentially taken up by hypoxic cells; and Secondly, β emitter transition metal atom (e.g., rhenium-186) complexed with a ligand vector that is preferentially taken up by the hypoxic cells, resulting in the radiotoxic effect sought.

Other advantageous aspects of the resent invention include:

providing new targeting anticancer agents in situ for treating primary and/or metastatic tumors;

providing new radiopharmaceutical agents for the diagnosis of primary and/or metastatic tumors; and providing new diagnostic agents for profiling hypotoxic tumors that do not respond to conventional anticancer therapies.

Advantageously, the inventive method described herein is particularly adapted for systemic therapy against metastases or inoperable or nonresponding tumors, resistant to conventional treatments.

1) General Description of Dendrimer Conjugates of the Invention

It was discovered that a pharmaceutical compound formed with a dendrimer-based supravector, combined with a transition metal/nitroimidazole ligand complex can prove useful for in situ anticancer therapy targeting hypotoxic tumors that are resistant to conventional treatment.

Advantageously, the compounds of the invention include a dendrimer conjugate (A) comprising a G2 to G10 polylysine dendrimer conjugated with a nitroimidazole ligand/metal complex having the following structure:

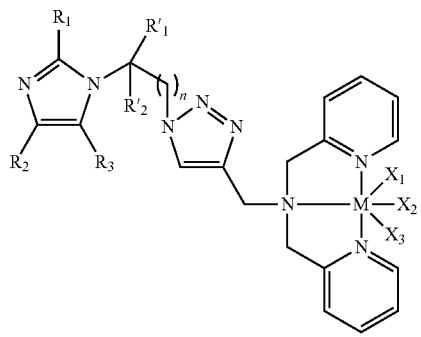

wherein n is an integer from 0 to 8 inclusive;

R1, R2 and R3 independently represent H, $NO_2$ or methyl;

R'1 and R'2 independently represent H, OH, methyl, ethyl or propyl;

X1, X2 and X3 independently represent ø, CO or $H_2O$ as allowed by the valence of metal M; and M represents a radioactive or non radioactive (cold) isotope of a transition metal selected from Y, Zr, Nb, Mo, Tc, Ru, Rh, Pd, Ag, Cd, Re, In or Sn.

Advantageously, the compounds of the invention include a dendrimer conjugate (B) comprising a G2 to G10 cyclotriphosphazene core phenoxymethyl(methylhydrazono)dendrimer conjugated with a ligand/metal complex combining a tetradentate 2-aminocyclopenten-dithiocarboxylate ligand coupled with an imidazolyl group and a metal, the ligand/metal complex having the following structure:

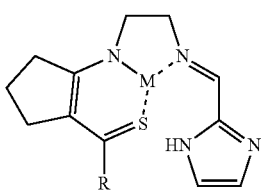

wherein

M represents a radioactive or non radioactive (cold) isotope of a transition metal selected from Y, Zr, Nb, Mo, Tc, Ru, Rh, Pd, Ag, Cd, Re, In or Sn; and R represents a linear or branched C1-6alkyl or C1-6heteroalkyl moiety, preferably -Me, —CH$_2$Ph or —CH(CH$_3$)OEt.

It is to be understood that all the embodiments that follow may apply to dendrimer conjugates (A) and/or (B), as defined above. Advantageously, the conjugation between the dendrimer an the ligand/metal complex may be non-covalent, so as to ensure release of the ligand/metal complex in the subject and/or in the cells upon administration of the dendrimer conjugate according to the invention.

Advantageously, the inventive dendrimer conjugates, deposited in situ as an in situ release vehicle, may comprise a polylysine or cyclotriphosphazene core phenoxymethyl (methylhydrazono)dendrimer (D) loaded with transition metal/imidazole ligand complexes (L-M complexes). The L-M complexes comprise two distinct parts: (i) an imidazolyl, nitroimidazolyl or methyl-imidazolyl moiety, and (ii) a transition metal chelating site (e.g., di(2-picolyl)-amine or tetradentate 2-aminocyclopenten-dithiocarboxylate). Thus, part (i) targets hypotoxic cells (resistant to conventional treatments), and part (ii) exhibits the pharmacological/therapeutic activity via the chelated transition metal (radioactivity or alkylating activity). Advantageously, dendrimer conjugates (A) combine a polylysine dendrimer (D) loaded with transition metal/imidazole ligand complexes (L-M complexes) comprising (i) an imidazolyl, nitroimidazolyl or methyl-imidazolyl moiety, and (ii) a di(2-picolyl)-amine transition metal chelating site. Advantageously, dendrimer conjugates (B) combine a cyclotriphosphazene core phenoxymethyl (methylhydrazono)dendrimer (D) loaded with transition metal/imidazole ligand complexes (L-M complexes) comprising (i) an imidazolyl, nitroimidazolyl or methyl-imidazolyl (preferably imidazolyl) moiety, and (ii) a 2-aminocyclopenten-dithiocarboxylate transition metal chelating site.

Advantageously, when M may be a radioactive isotope, the dendrimer conjugates of the invention may be used for imaging and radiotherapy applications. In exemplary advantageous embodiments, M may represent $^{99m}$Tc or $^{186/188}$Re.

Advantageously, when M may be a non radioactive (cold) isotope, the dendrimer conjugates of the invention may be used for chemotherapy applications.

As referred to herein, dendrimers are synthetic polymers characterized by repeated chain branchings emanating from a central core, giving rise to a fractal-like topology and a large number of chain endings. Dendrimers are composed of a core, one or more layers (or generations) of branched monomers, and a layer of end-groups that double each "generation" and terminate the various chains.

Generation, G, refers to the number of layers in the dendrimer, and Z is the number of end groups on the dendrimer outer surface. As used herein, the core is generation 0 (G0). A monomer directly attached to the core can be considered a 1st generation monomer (G1); a monomer attached to a G1 monomer is a 2nd generation monomer (G2), etc. In this system of numbering $Z=2^{(G+1)}$. Thus, for a dendrimer where the core has 2 functional groups, for G0 $Z=2(2^{(0+1)})$, for G1 $Z=4$ $(2^{(1+1)})$, etc.

Advantageously, the dendrimer has a generation value of at least 2, where the core is assigned generation zero. For example, the dendrimer may have a generation value of 2, 3, 4, 5, 6, 7, 8, 9 or 10. Advantageously, the dendrimer may have a generation value of 2, 3, 4, 5, 6, 7; preferably 3, 4, 5; most preferably 5.

Exemplary dendrimers include dendrimeric forms of poly-L-lysine (PLL). These may be advantageously used for dendrimer conjugates (A).

Other exemplary dendrimers include cyclotriphosphazene core phenoxymethyl(methylhydrazono) dendrimers. These may be advantageously used for dendrimer conjugates (B).

With increasing generations, dendrimers develop through a continuum of molecular shapes ranging from open, extended structures to ellipsoids, to closed globular spheroids. Since the number of ends increase exponentially with generation, and surface area increases with the square, steric crowding of the branches at high generations results in a crowded surface; after about G5 (Z=64) there is a decrease in accessibility of the ends and thus their reactivity. The high surface and relatively lower interior densities of larger dendrimers supports cavities with diameters ranging from 5 to 15 Angstrom that may be joined to channels connecting to the surface.

For example, the dendrimer according to the invention may be depicted as follows:

(D)

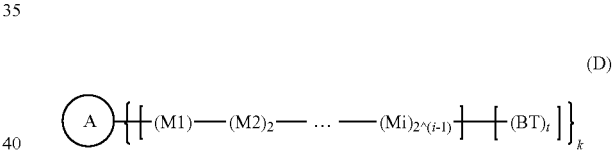

wherein:

(a) A represents the dendrimer's core, of multivalency k, wherein:

k represents the number of dendrons and is preferably 3;

A represents a core synthon having the following structure:

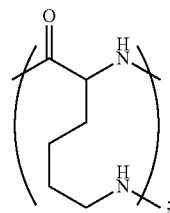

(b) Mi represents a monomer of generation i, wherein:

i is an integer from 2 to g, g being the generation number of the dendrimer;

when i=0, Mi represents ø, and the terminal branch BT is then directly bound to the core synthon A;

when i>0, Mi represents:

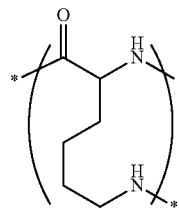

wherein the symbol * denotes the attachment point of monomer Mi with the monomer of the next generation;

(c) BT represents a terminal branch, and t the number of terminal moieties wherein:

t is an integer from 1 to 3, preferably t is 2 or 3;

each occurrence of BT independently represents a hydrogen atom, a carboxyl moiety (COOH), a carboxylate ester (COO—R), a hydroxyl group (OH); a thiol group (SH) or a thiol ester moiety (S—R) wherein each occurrence of R independently represents a C1-C6alkyl or C6 aryl group.

The generation g may range from 2 to 10. In certain advantageous embodiments, g may be 2, 3, 4 or 5; preferably g may be 2 or 3; most preferably g may be 2.

Advantageously, in the dendrimer conjugate, said conjugation comprises, ionic bonds, metallic bonds, hydrogen bonds, or Van der Waals bonds.

Advantageously, in the dendrimer conjugate, the dendrimer may have the following structure:

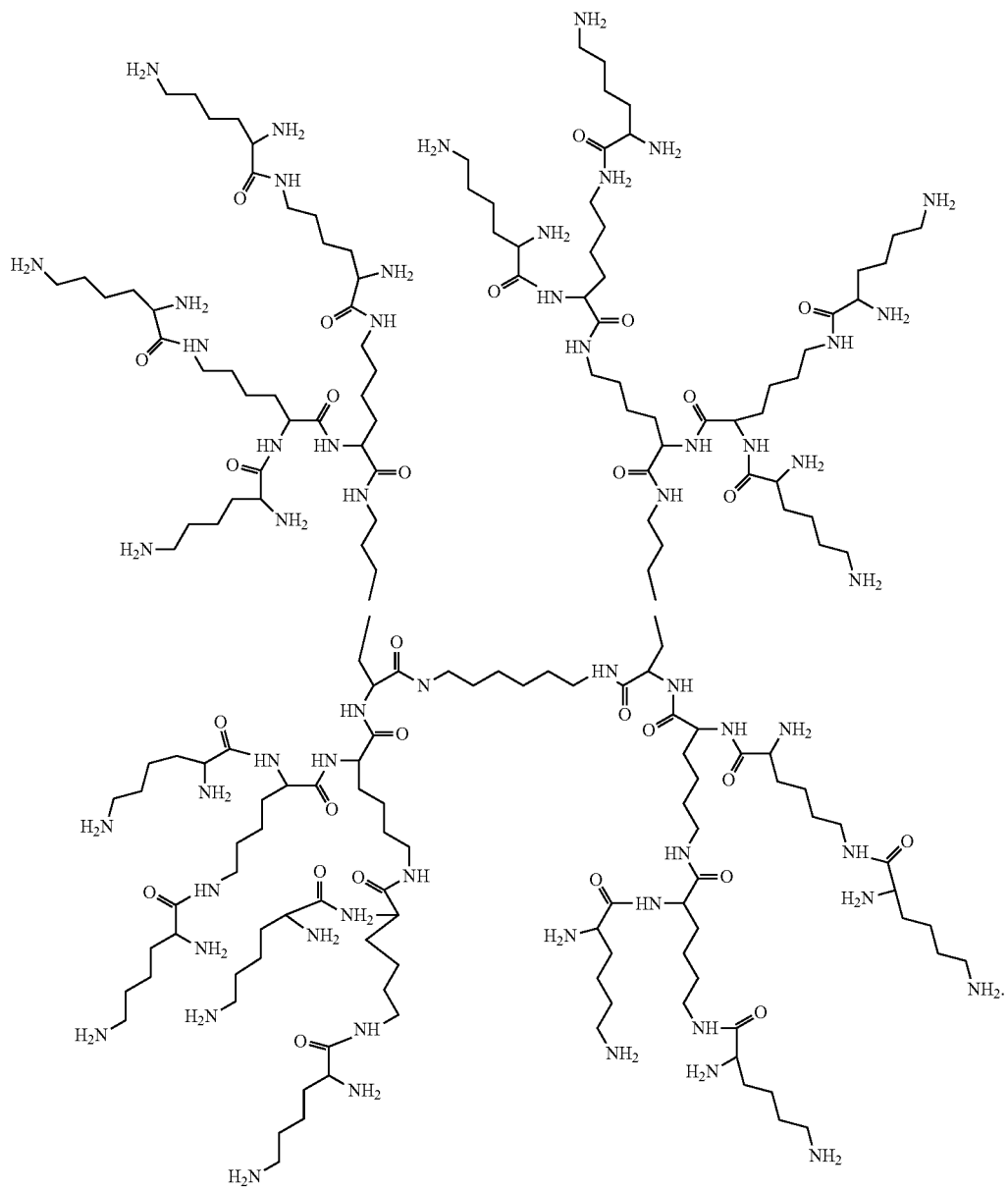

Advantageously, in the dendrimer conjugate, the nitroimidazole ligand/metal complex has the following structure:

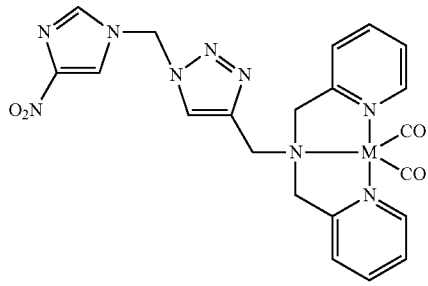

wherein M represents a radioactive or non radioactive (cold) isotope of a transition metal selected from Y, Zr, Nb, Mo, Tc, Ru, Rh, Pd, Ag, Cd, Re, In or Sn.

Advantageously, in the dendrimer conjugate, the nitroimidazole ligand/metal complex has the following structure:

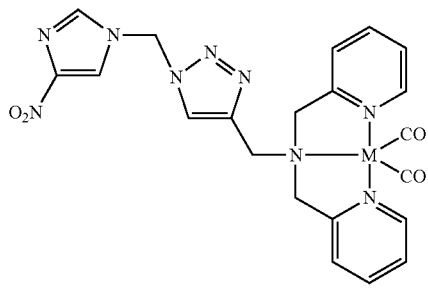

wherein M represents a non radioactive (cold) isotope of a transition metal selected from Y, Zr, Nb, Mo, Tc, Ru, Rh, Pd, Ag, Cd, Re, In or Sn. Advantageously, the resulting dendrimer conjugate may be used for chemotherapy applications.

Advantageously, in the dendrimer conjugate, the nitroimidazole ligand/metal complex has the following structure:

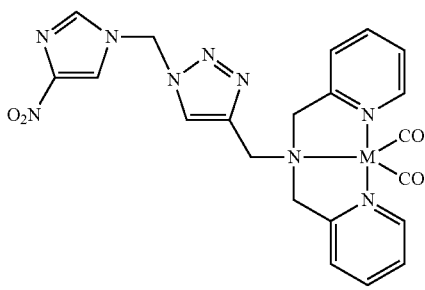

wherein M represents $^{99m}$Tc or $^{186/188}$Re. Advantageously, the resulting dendrimer conjugate may be used for radiotherapy applications.

The dendrimer conjugate of claim 1 or 2, wherein the conjugate has the following structure:

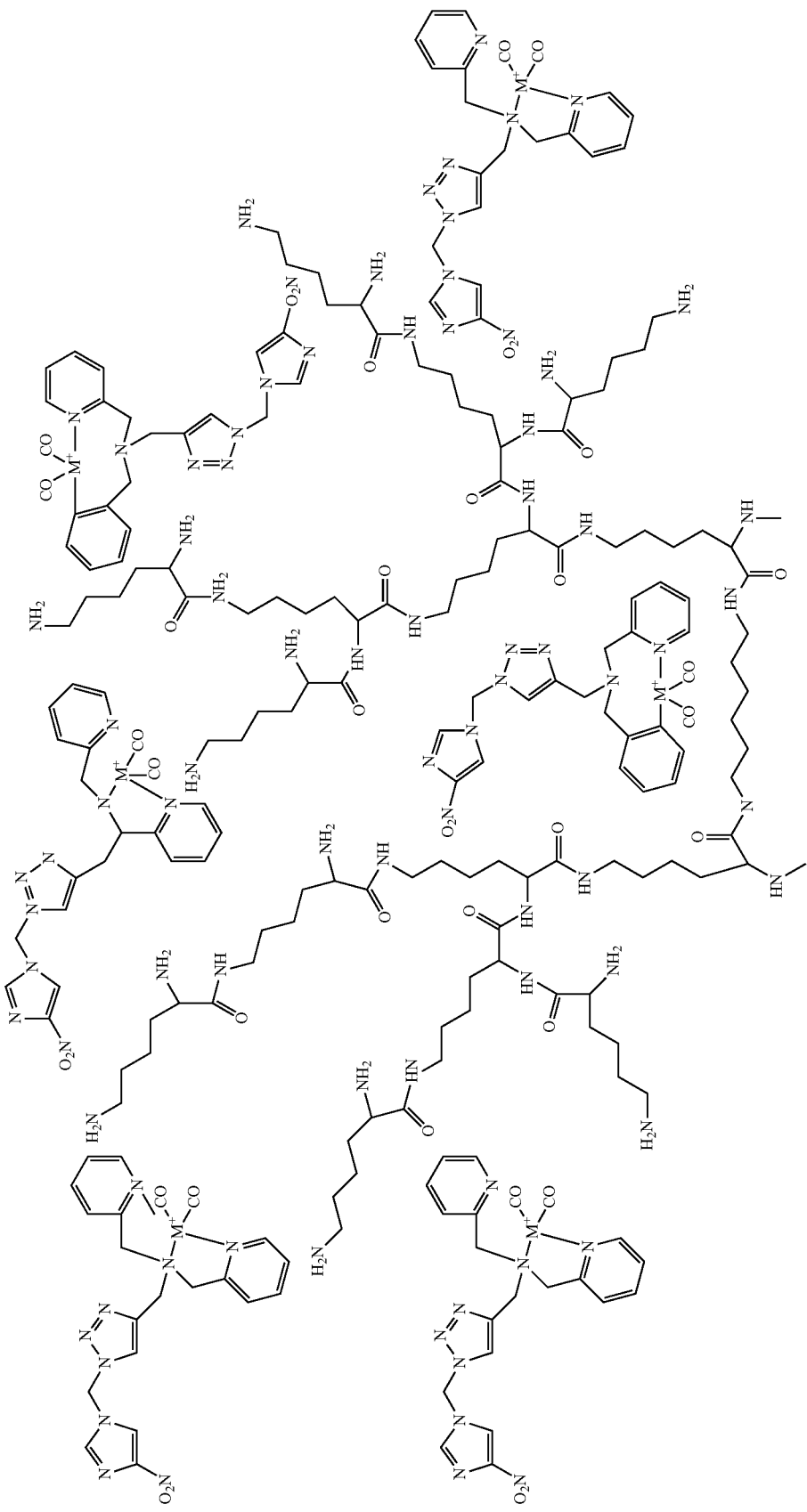

-continued
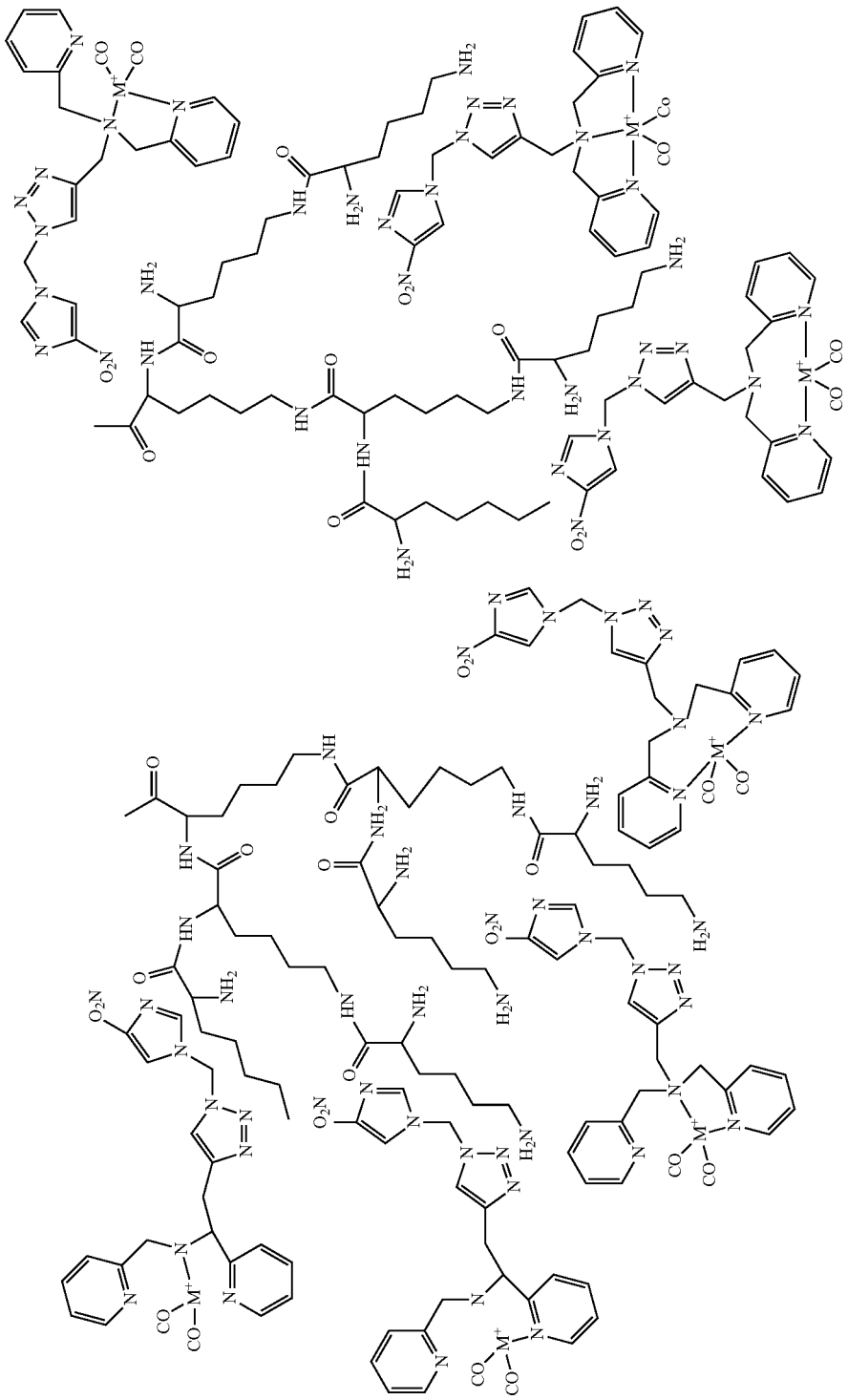

wherein M represents $^{99}$Tc or $^{186}$Re.

Some of the foregoing compounds can comprise one or more asymmetric centers, and thus can exist in various isomeric forms, e.g., stereoisomers and/or diastereomers. Thus, inventive compounds and pharmaceutical compositions thereof may be in the form of an individual enantiomer, diastereomer or geometric isomer, or may be in the form of a mixture of stereoisomers. In certain embodiments, the compounds of the invention are enantiopure compounds. In certain other embodiments, mixtures of stereoisomers or diastereomers are provided.

2) Synthetic Overview:

The practitioner has a well-established literature of dendrimer chemistry to draw upon, in combination with the information contained herein, for guidance on synthetic strategies, protecting groups, and other materials and methods useful for the synthesis of the dendrimer conjugates of this invention.

General Synthetic Methods:

Ligand Synthesis

The chloro-alkyl-nitroimimidazol compound (2) may be obtained by adding the amine function on the chloroalkyl imidazole (1). The azido-alkyl-nitroimidazol compound (3) may be obtained by substitution of the chlorine atom by an azide group. The final compound Nitro-Imidazole-alkyl-1,2,3-triazol-methyl-di-(2-picolyl)amine (5) may be obtained by dissolving propargyl di-(2-picolyl)amine (4) with the azido-alkyl-nitruroimidazol compound (3) in a solvent mixture dioxane/water at 100° C. in the presence of copper sulfate and sodium ascorbate, as shown in Scheme 1A below:

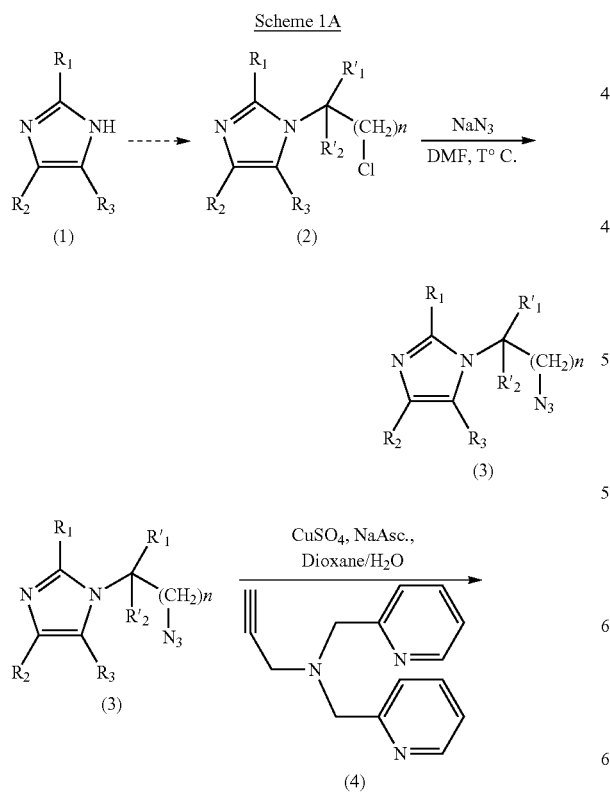

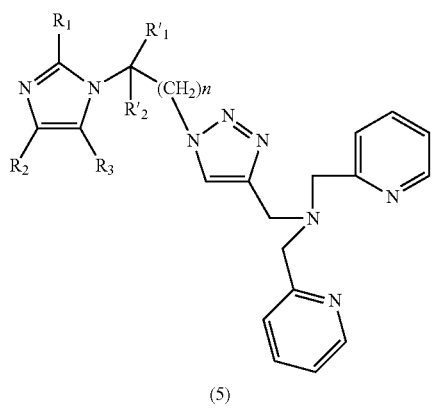

R1 = H, NO2, CH3
R2 = H, NO2, CH3
R1 = H, NO2, CH3
N = 1-8
R'1 = H, OH, CH3, C2H5, C3H7,
R'2 = H, CH3, CH3, C2H5, C3H7

An exemplary synthesis of tetradentate methyl 2-aminocyclopentene-1-dithiocarboxylate imidazolyl ligand is shown in Scheme 1B below:

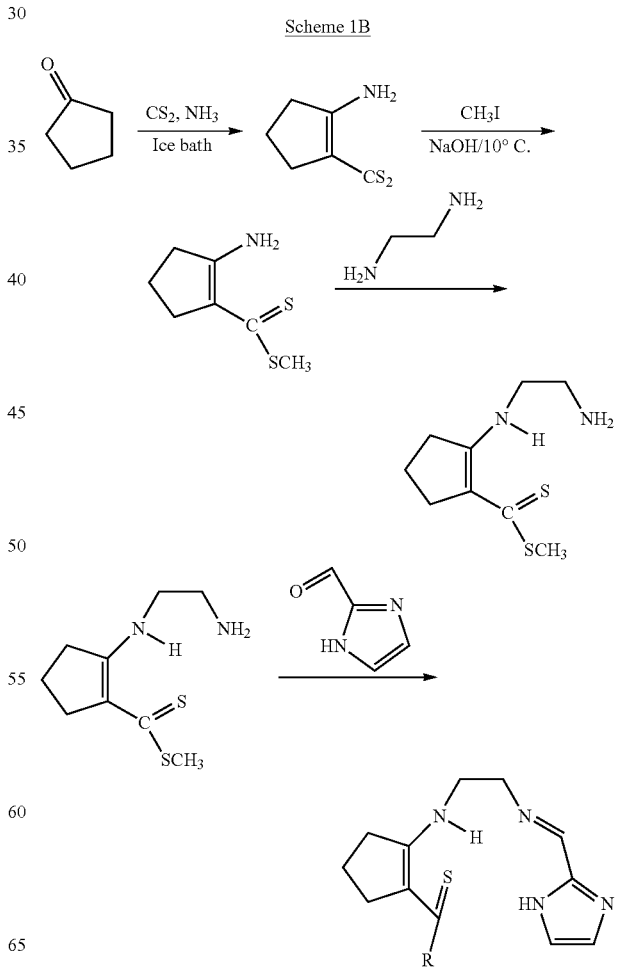

where R represents a linear or branch C1-6alkyl or C1-6heteroalkyl moiety, preferably -Me, —CH$_2$Ph or —CH(CH$_3$)OEt.

Dendrimer

Polylysine dendrimers suitable for carrying out the invention are commercially available (for example, G10 polylysine dendrimer may be purchased from the company Colcom, Montpellier, France; or from Sigma-Aldrich).

Cyclotriphosphazene core phenoxymethyl(methylhydrazono) dendrimers suitable for carrying out the invention are also commercially available (for example, cyclotriphosphazene phenoxymethyl(methylhydrazono) dendrimer generation 1.5 may be purchased from Sigma-Aldrich).

In addition, The various patent documents and other references cited herein provide helpful background information on preparing compounds similar to the inventive dendrimer conjugates described herein or relevant intermediates. Certain cited patent documents also contain information on formulation, uses, and administration of such dendrimer conjugates which may be of interest.

Numerous U.S. patents describe methods and compositions for producing dendrimers. Thus, dendrimer chemistry is widely known, as evidenced by the various patent documents referenced below, which may be adapted, or at least provide some guidance, for synthetic strategies to prepare polylysine dendrimers.

Examples of some of these patents are given below in order to provide a description of some dendrimer compositions that may be useful in the present invention, however it should be understood that these are merely illustrative examples and numerous other similar dendrimer compositions could be used in the present invention.

U.S. Pat. Nos. 4,507,466, 4,558,120, 4,568,737, and 4,587,329 each describe methods of making dense star polymers with terminal densities greater than conventional star polymers. These polymers have greater/more uniform reactivity than conventional star polymers, i.e. 3rd generation dense star polymers. These patents further describe the nature of the amidoamine dendrimers and the 3-dimensional molecular diameter of the dendrimers.

U.S. Pat. No. 4,631,337 describes hydrolytically stable polymers. U.S. Pat. No. 4,694,064 describes rod-shaped dendrimers. U.S. Pat. No. 4,713,975 describes dense star polymers and their use to characterize surfaces of viruses, bacteria and proteins including enzymes. Bridged dense star polymers are described in U.S. Pat. Nos. 4,737,550, 4,857,599 and 4,871,779 describe dense star polymers on immobilized cores useful as ion-exchange resins, chelation resins and methods of making such polymers U.S. Pat. No. 5,338,532 is directed to starburst conjugates of dendrimer(s) in association with at least one unit of carried agricultural, pharmaceutical or other material. This patent describes the use of dendrimers to provide means of delivery of high concentrations of carried materials per unit polymer, controlled delivery, targeted delivery and/or multiple species such as e.g., drugs antibiotics, general and specific toxins, metal ions, radionuclides, signal generators, antibodies, interleukins, hormones, interferons, viruses, viral fragments, pesticides, and antimicrobials.

U.S. Pat. No. 6,471,968 describes a dendrimer complex comprising covalently linked first and second dendrimers, with the first dendrimer comprising a first agent and the second dendrimer comprising a second agent, wherein the first dendrimer is different from the second dendrimer, and where the first agent is different than the second agent.

Other useful dendrimer type compositions are described in U.S. Pat. Nos. 5,387,617, 5,393,797, and 5,393,795 in which dense star polymers are modified by capping with a hydrophobic group capable of providing a hydrophobic outer shell. U.S. Pat. No. 5,527,524 discloses the use of amino terminated dendrimers in antibody conjugates.

The use of dendrimers as metal ion carriers is described in U.S. Pat. Nos. 5,560,929, 5,773,527 discloses non-cross-linked polybranched polymers having a comb-burst configuration and methods of making the same. U.S. Pat. No. 5,631,329 describes a process to produce polybranched polymer of high molecular weight by forming a first set of branched polymers protected from branching; grafting to a core; deprotecting first set branched polymer, then forming a second set of branched polymers protected from branching and grafting to the core having the first set of branched polymers, etc.

The reader can draw from the above-cited patent references to adapt synthetic methods to prepare dendrimer conjugates according to the invention.

Generally speaking, in dendrimer chemistry, different generation layers may be obtained in successive generations by various methods of the divergent type (if one starts with the core) or convergent type (if one starts from one or several generation branches) in one or several steps. The dendrimers each generation, i.e. having a determined number of layers, may be isolated. The different generation layers (either internal or external) may be, like the core, organic, inorganic or consist of organic and inorganic elements.

The construction of these dendrimers may be strictly controlled. For example, in order to build a dendrimer, a series of generation branches may be attached to the core and may form a first generation layer (generation 1) including at the periphery the same external functions and, by repeating the sequence of reactions used for building the first generation, a second generation layer is attached (generation 2) and then a third, a fourth, etc. . . .

The last generation layer (generation g) consists of chains of generation g. It comprises a plurality of identical chemical functions distributed at the periphery, each function forming or extending the free end of one of said generation branches of the last layer. At the end of these chains of generation g, intermediate chains may then be grafted, for example with PEG chains, to odulate the pharmacokinetic profile of the dendrimer conjugate.

Dendrimers may be characterized by a number of techniques including, but not limited to, electrospray-ionization mass spectroscopy, $^{13}$C nuclear magnetic resonance spectroscopy, $^{1}$H nuclear magnetic resonance spectroscopy, high performance liquid chromatography, size exclusion chromatography with multi-angle laser light scattering, ultraviolet spectrophotometry, capillary electrophoresis and gel electrophoresis. These tests assure the uniformity of the polymer population and are important for monitoring quality control of dendrimer manufacture for applications and in vivo usage.

Moreover, the practitioner is directed to the specific guidance and examples provided in this document relating to various exemplary compounds and intermediates thereof.

Complexation of the Dendrimer-ligand Compound with a Transition Metal M

The metal complexation at the ligand complexation site aims at activating the dendrimer-ligand compound. For example, this activation may be effected by incubating the dendrimer-ligand compound with a hydrated carbonylmetalated compound M(CO)$_3$(H$_2$O)$_3$, as illustrated in Scheme 3.

Scheme 3. Ligand activation by formation of ligand-metal complex

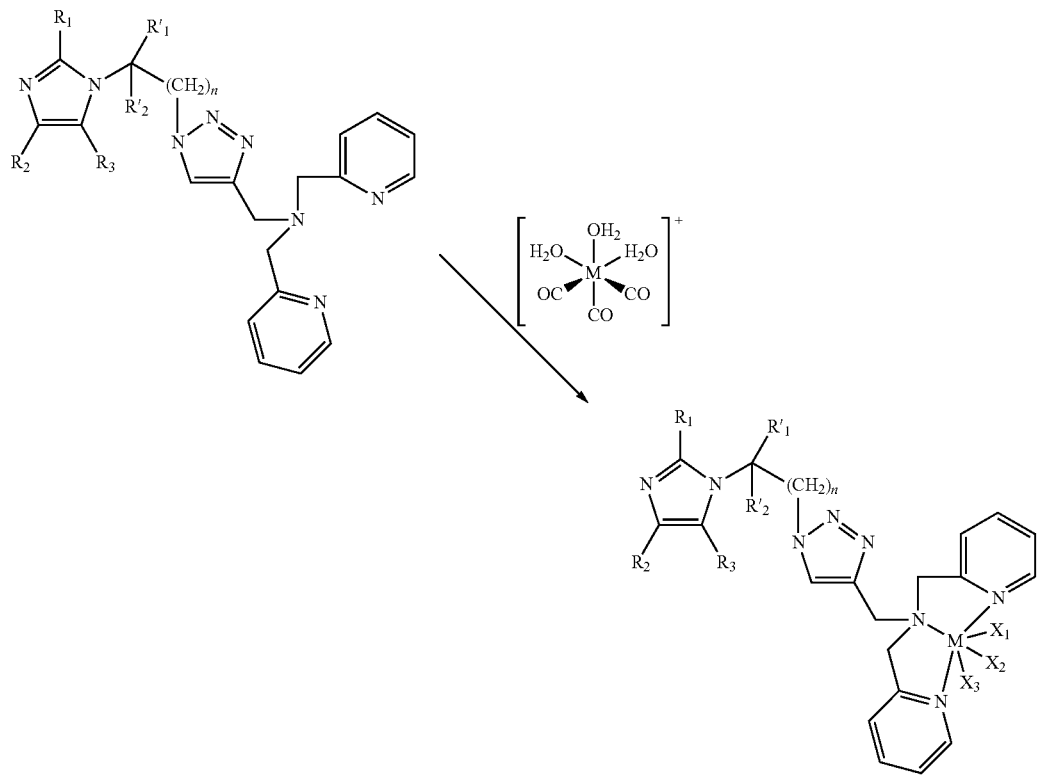

R1 = H, NO2, CH3
R2 = H, NO2, CH3
R1 = H, NO2, CH3
N = 1-8
R'1 = H, OH, CH3, C2H5, C3H7
R'2 = H, CH3, CH3, C2H5, C3H7

X1 = X2 = X3 = CO, H2O

M = Transition Metal
Y (Yttrium); Zr(Zirconium); Nb (Niobium); Mo (Molybdène); Technétium);
Ru (Ruthénium); Rh (Rhodium); Pd (Palladium); Ag (Argent); Cd (Cadmium);
Re (Rhénium); In (Indium); Sn (Étain)

Below is illustrated an exemplary synthesis for the formation of a complex between metal M and tetradentate methyl 2-aminocyclopentene-1-dithiocarboxylate imidazolyl ligand:

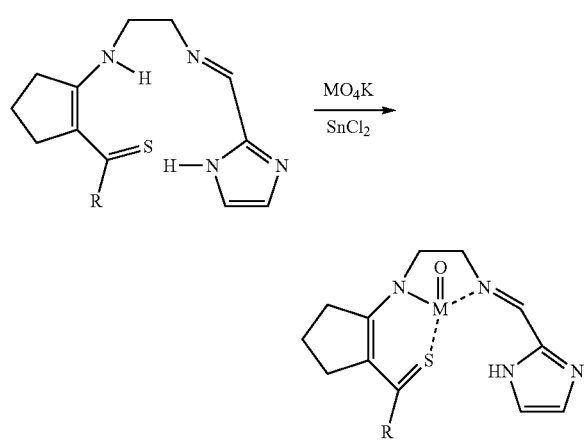

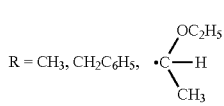

$R = CH_3, CH_2C_6H_5,$

M = Tc or Re

Similarly to activate the dendrimer-ligand compound with rhenium (for therapy) or technetium (for diagnosis) obtained after elution of generators in the form of perrhenates ($ReO_4$) or pertechnetate ($TcO_4$), other reducing agents can be used and especially tin chloride ($SnCl_2$) or phosphines (Technetium-99m and rhenium complexes with new polydentates ligands derived from dithiocarboxylic acid. Improvement of oxo and nitrido-technetium radiopharmaceuticals for regional blood flow evaluation; H. BELHADJ-TAHAR, PhD Thesis, University Grenoble 1; 1996).

3) Pharmaceutical Compositions

As discussed above, the present invention provides dendrimer conjugates that are useful as medicament in the treatment or diagnosis of cancer. All the embodiments that follow apply to dendrimer conjugates (A) and/or (B), as defined herein.

Accordingly, in another aspect of the present invention, pharmaceutically acceptable compositions are provided, wherein these compositions comprise any of the dendrimer conjugates as described herein, and optionally comprise a pharmaceutically acceptable carrier, adjuvant or vehicle. In certain embodiments, these compositions optionally further comprise one or more additional therapeutic agents.

Advantageously, the composition according to the invention comprises a dendrimer conjugate, wherein M is a radioactive isotope as defined above, such as $^{186/188}$Re and the composition is a radiopharmaceutical composition.

Advantageously, the composition according to the invention comprises a dendrimer conjugate, wherein M is a radioactive isotope as defined above, such as $^{99m}$Tc and the composition is a diagnostic composition.

In advantageous embodiments, the dendrimer conjugates are used in conjunction with appropriate salts and buffers to render delivery of the compositions in a stable manner to allow for uptake by target cells. Buffers also may be employed when the dendrimer conjugates are introduced into a patient. Aqueous compositions comprise an effective amount of the dendrimer conjugates to cells dispersed in a pharmaceutically acceptable carrier or aqueous medium. Such compositions also are referred to as inocula. The phrase "pharmaceutically or pharmacologically acceptable" refer to molecular entities and compositions that do not produce adverse, allergic, or other untoward reactions when administered to an animal or a human. As used herein, "pharmaceutically acceptable carrier" includes any and all solvents, dispersion media, coatings, antibacterial and antifungal agents, isotonic and absorption delaying agents and the like. Except insofar as any conventional media or agent is incompatible with the vectors or cells of the present invention, its use in therapeutic compositions is contemplated. Supplementary active ingredients may also be incorporated into the compositions.

Advantageously, the inventive compositions may include classic pharmaceutical preparations. Administration of these compositions according to the present invention may be effected via any common route so long as the target tissue is available via that route. This includes, but is not limited to, intradermal, intraperitoneal or intravenous injection. The dendrimer conjugates may also be administered parenterally or intraperitoneally or intratumorally.

Solutions of the dendrimer conjugates as free base or pharmacologically acceptable salts may be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations may contain a preservative to prevent the growth of microorganisms.

The pharmaceutical forms suitable for injectable use include sterile aqueous solutions or dispersions and sterile powders for the extemporaneous preparation of sterile injectable solutions or dispersions. The carrier may be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial an antifungal agents, for example, parabens, chlorobutanol, phenol, sorbic acid, thimerosal, and the like. In many cases, it may be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions may be prepared by incorporating the dendrimer conjugates in the required amount in the appropriate solvent with various of the other ingredients enumerated above, as required, followed by filtered sterilization. Generally, dispersions may be prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation include vacuum-drying and freeze-drying techniques which yield a powder of the active ingredient plus any additional desired ingredient from a previously sterile-filtered solution thereof.

Upon formulation, dendrimer conjugates may be administered in a manner compatible with the dosage formulation and in such amount as is therapeutically effective. The formulations may be easily administered in a variety of dosage forms such as injectable solutions. For parenteral administration in an aqueous solution, for example, the solution may be suitably buffered, if necessary, and the liquid diluent first rendered isotonic with sufficient saline or glucose. These particular aqueous solutions may especially be suitable for intravenous and intraperitoneal administration. For example, one dosage could be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580).

As described above, the pharmaceutically acceptable compositions of the present invention additionally comprise a pharmaceutically acceptable carrier, adjuvant, or vehicle, which, as used herein, includes any and all solvents, diluents, or other liquid vehicle, dispersion or suspension aids, surface active agents, isotonic agents, preservatives, and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention.

Uses of Dendrimer Conjugates and Pharmaceutically Acceptable Compositions

The dendrimer conjugates of the present invention may find use in the detection and treatment of a variety of cancers. Thus, in one aspect, the invention provides dendrimer conjugates as described herein for use as a medicament in the treatment or diagnosis of cancer. Therefore, there is provided dendrimer conjugates as described herein, or pharmaceutical compositions thereof, for use as a medicament in the treatment or diagnosis of cancer. Thus, there is provided a method for treating or for diagnosing cancer, comprising administering to a subject in need thereof an effective amount of a dendrimer conjugate according to the invention, or pharmaceutical compositions thereof.

In yet another aspect, a method for the treatment or lessening the severity of cancer is provided comprising administering an effective amount of a dendrimer conjugate, or a pharmaceutically acceptable composition comprising a dendrimer conjugate to a subject in need thereof. Therefore, there is provided dendrimer conjugates as described herein, or pharmaceutical compositions thereof, for use as a medicament for treating or lessening the severity of cancer. In certain embodiments of the present invention an "effective amount" of the dendrimer conjugate or pharmaceutically acceptable composition is that amount effective for treating or lessening the severity of cancer. The dendrimer conjugates and compositions, according to the method of the present invention, may be administered using any amount and any route of administration effective for treating or lessening the severity of cancer. The exact amount required will vary from subject to subject, depending on the species, age, and general condition of the subject, the severity of the infection, the particular agent, its mode of administration, and the like. The compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the dendrimer conjugates and compositions of the present invention will be decided by the attending physician within the scope of sound medical judgment. The specific effective dose level for any particular patient or organism will depend upon a variety of factors including the cancer being treated and the severity of the cancer; the activity of the specific dendrimer conjugate employed; the specific composition employed; the age, body weight, general health, sex and diet of the patient; the time of administration, route of administration, and rate of excretion of the specific dendrimer conjugate employed; the duration of the treatment; drugs used in combination or coincidental with the specific dendrimer conjugate employed, and like factors well known in the medical arts. The term "patient", as used herein, means an animal, preferably a mammal, and most preferably a human.

Advantageously, M may be a radioactive isotope, such as $^{186/188}$Re, and the dendrimer conjugate composition is a radiopharmaceutical composition. Thus, there also is provided a method of treating cancer comprising administering to a subject suffering from or susceptible to said cancer a therapeutically effective amount of a radiopharmaceutical composition according to the invention, wherein M may be a radioactive isotope as defined herein, such as $^{186/188}$Re. For example, said cancer may be selected from the group consisting of lymphoma, Hodgkin's disease, non-Hodgkin's disease, Multiple myeloma, Waldenstrom's macroglobulinemia, Heavy chain disease, solid tumors, sarcomas and carcinomas, fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, brain cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, uterine cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, and neuroblastomaretinoblastoma and all solid tumors.

Advantageously, the step of administering comprises injecting the composition intraarterially through interventional radiography, intratumorally or peritumorally, and all kind of administration achieving in situ deposition of the therapeutic agent (dendrimer conjugate). Advantageously, the step of administering a therapeutically effective amount of the composition comprises administering a dose between about 37 MBq/kg of $^{188}$Re corresponding to 5,4 $10^{-12}$ mol metal/kg of the subject's body weight and about 68 MBq/kg of $^{188}$Re corresponding to 9,96 $10^{-12}$ mol metal/kg of the subject's body weight.

In advantageous embodiments, there is provided a method of altering tumor growth in a subject, comprising: a) providing a composition comprising a dendrimer conjugate according to the invention and b) administering to a subject in need thereof a therapeutically effective amount of said composition under conditions such that said tumor growth is altered. For example, said altering comprises inhibiting tumor growth in said subject. In yet another example, said altering comprises reducing the size of said tumor in said subject. The tumor may be a primary or metastatic tumor. Thus, there is provided dendrimer conjugates according to the invention, or pharmaceutical compositions thereof, for use as medicament for altering tumor growth in a subject.

In another aspect, there is provided a method for lymphatic system imaging, comprising: administering to a subject an image enhancing amount of a dendrimer conjugate according to the invention, wherein the metal M is $^{99m}$Tc; and detecting a difference in an image signal intensity of at least a portion of the lymphatic system after the dendrimer conjugate is administered, wherein the difference in image signal intensity indicates the presence of metastatic cancer cells. Advantageously, the portion of the lymphatic system may comprise a lymph node. Advantageously, the administering step may comprise injecting the composition intravenously or intralymphatically. Advantageously, the step of administering an imaging enhancing amount of the dendrimer conjugate comprises administering a dose between about 10.5 MBq of $^{99m}$Tc corresponding to 0.6 $10^{-12}$ mol metal/kg of the subject's body weight and about 26.3 MBq of $^{99m}$Tc corresponding to 1.5 $10^{-12}$ mol metal/kg of the subject's body weight. Thus, there is provided dendrimer conjugates according to the invention, or pharmaceutical compositions thereof, for use as medicament for lymphatic system imaging.

Dosage ranges for radioisotopes vary widely, and depend on the half-life of the isotope, the strength and type of radiation emitted, and the uptake by the neoplastic cells. The skilled artisan is directed to "Remington's Pharmaceutical Sciences" 15th Edition, chapter 33, in particular pages 624-652. Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by regulatory administrations (e.g., FDA Office of Biologics standards in the United States).

In advantageous embodiments of the present invention, the in situ delivery of the dendrimer conjugates to patients with cancers may be utilized to maximize the therapeutic effectiveness of the delivered agent. Similarly, the chemo- or radiotherapy may be directed to particular, affected region of the subjects body. Alternatively, systemic delivery of the dendrimer conjugate composition and/or the agent may be appropriate in certain circumstances, for example, where extensive metastasis has occurred.

An attractive feature of the present invention is that the therapeutic compositions may be delivered to local sites in a patient by a medical device. Medical devices that are suitable for use in the present invention include known devices for the localized delivery of therapeutic agents. Such devices include, but are not limited to, catheters such as injection catheters, balloon catheters, double balloon catheters, microporous balloon catheters, channel balloon catheters, infusion catheters, perfusion catheters, etc., which are, for example, coated with the therapeutic agents or through which the agents are administered; needle injection devices such as hypodermic needles and needle injection catheters; needleless injection devices such as jet injectors; coated stents, bifurcated stents, vascular grafts, stent grafts, etc.; and coated vaso-occlusive devices such as wire coils.

Exemplary devices are described in U.S. Pat. Nos. 5,935,114; 5,908,413; 5,792,105; 5,693,014; 5,674,192; 5,876,445; 5,913,894; 5,868,719; 5,851,228; 5,843,089; 5,800,519; 5,800,508; 5,800,391; 5,354,308; 5,755,722; 5,733,303; 5,866,561; 5,857,998; 5,843,003; and 5,933,145; the entire contents of which are incorporated herein by reference. Exemplary stents that are commercially available and may be used in the present application include the RADIUS (SCIMED LIFE SYSTEMS, Inc.), the SYMPHONY (Boston Scientific Corporation), the Wallstent (Schneider Inc.), the PRECEDENT II (Boston Scientific Corporation) and the NIR (Medinol Inc.). Such devices are delivered to and/or implanted at target locations within the body by known techniques.

Where clinical applications are contemplated, in some embodiments of the present invention, the dendrimer conjugates are prepared as part of a pharmaceutical composition in a form appropriate for the intended application. Generally, this entails preparing compositions that are essentially free of pyrogens, as well as other impurities that could be harmful to humans or animals. However, in some embodiments of the present invention, a straight dendrimer formulation may be administered using one or more of the routes described herein.

Advantageously, the pharmaceutically acceptable compositions of this invention may be administered to humans and other animals by injecting the composition intraarterially through interventional radiography, intratumorally or peritumorally, intravenously or intralymphatically, and all kind of administration achieving in situ deposition of the therapeutic agent.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid may be used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

Combination Therapy

It will also be appreciated that the dendrimer conjugates and pharmaceutically acceptable compositions of the present invention can be employed in combination therapies, that is, the dendrimer conjugates and pharmaceutically acceptable compositions can be administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an inventive dendrimer conjugates may be administered concurrently with another agent used to treat the same disorder), or they may achieve different effects (e.g., control of any adverse effects). As used herein, additional therapeutic agents that are normally administered to treat or prevent a particular disease, or condition, are known as "appropriate for the disease, or condition, being treated".

For example, other therapies, chemotherapeutic agents or other anti-proliferative agents may be combined with the dendrimer conjugates of this invention to treat proliferative diseases and cancer. Examples of therapies or anticancer agents that may be used in combination with the inventive anticancer agents of the present invention include surgery, radiotherapy (in but a few examples, gamma-radiation, neutron beam radiotherapy, electron beam radiotherapy, proton therapy, brachytherapy, and systemic radioactive isotopes, to name a few), endocrine therapy, biologic response modifiers (interferons, interleukins, and tumor necrosis factor (TNF) to name a few), hyperthermia and cryotherapy, agents to attenuate any adverse effects (e.g., antiemetics), and other approved chemotherapeutic drugs, including, but not limited to, alkylating drugs (mechlorethamine, chlorambucil, Cyclophosphamide, Melphalan, Ifosfamide), antimetabolites (Methotrexate), purine antagonists and pyrimidine antagonists (6-Mercaptopurine, 5-Fluorouracil, Cytarabile, Gemcitabine), spindle poisons (Vinblastine, Vincristine, Vinorelbine, Paclitaxel), podophyllotoxins (Etoposide, Irinotecan, Topotecan), antibiotics (Doxorubicin, Bleomycin, Mitomycin), nitrosoureas (Carmustine, Lomustine), inorganic ions (Cisplatin, Carboplatin), enzymes (Asparaginase), and hormones (Tamoxifen, Leuprolide, Flutamide, and Megestrol), Gleevec™, adriamycin, dexamethasone, and cyclophosphamide. For a more comprehensive discussion of updated cancer therapies see, The Merck Manual, Nineteenth Ed. 2011, the entire contents of which are hereby incorporated by reference. See also the National Cancer Institute (CNI) website (www.nci.nih.gov) and the Food and Drug Administration (FDA) website for a list of the FDA approved oncology drugs (www.fda.gov/cder/cancer/druglistframe—See Appendix).

In advantageous embodiments, the dendrimer according to the invention may be conjugated with one or more anti-cancer agents.

Alternatively, or additionally, the composition comprising a dendrimer conjugate may be co-administered with a chemotherapeutic agent or anti-oncogenic agent. For example, the chemotherapeutic agent may be selected from the group consisting of platinum complex, verapamil, podophylltoxin, carboplatin, procarbazine, mechloroethamine, cyclophosphamide, camptothecin, ifosfamide, melphalan, chlorambucil, bisulfan, nitrosurea, adriamycin, dactinomycin, daunorubicin, doxorubicin, bleomycin, plicomycin, mitomycin, bleomycin, etoposide, tamoxifen, paclitaxel, taxol, transplatinum, 5-fluorouracil, vincristin, vinblastin, and methotrexate.

Treatment Kit

In other embodiments, the present invention relates to a kit for conveniently and effectively carrying out the methods in accordance with the present invention. In general, the pharmaceutical pack or kit comprises one or more containers filled with one or more of the ingredients of the pharmaceutical compositions of the invention. Such kits are especially suited for the delivery of injectable forms. Such a kit preferably includes a number of unit dosages, and may also include a card having the dosages oriented in the order of their intended use. If desired, a memory aid can be provided, for example in the form of numbers, letters, or other markings or with a calendar insert, designating the days in the treatment schedule in which the dosages can be administered. Optionally associated with such container(s) can be a notice in the form prescribed by a governmental agency regulating the manufacture, use or sale of pharmaceutical products, which notice reflects approval by the agency of manufacture, use or sale for human administration.

Equivalents

The representative examples that follow are intended to help illustrate the invention, and are not intended to, nor should they be construed to, limit the scope of the invention. Indeed, various modifications of the invention and many further embodiments thereof, in addition to those shown and described herein, will become apparent to those skilled in the art from the full contents of this document, including the examples which follow and the references to the scientific and patent literature cited herein. It should further be appreciated that the contents of those cited references are incorporated herein by reference to help illustrate the state of the art.

The following examples contain important additional information, exemplification and guidance that can be adapted to the practice of this invention in its various embodiments and the equivalents thereof.

EXEMPLIFICATION

The dendrimer conjugates of this invention and their preparation can be understood further by the examples that illustrate some of the processes by which these compounds are prepared or used. It will be appreciated, however, that these examples do not limit the invention. Variations of the invention, now known or further developed, are considered to fall within the scope of the present invention as described herein and as hereinafter claimed.

Example 1

Synthesis of 4-Nitro-1H-Imidazole-Methyl-1,2,3-Triazol-Methyl-Di-(2-Pycolyl)Amine

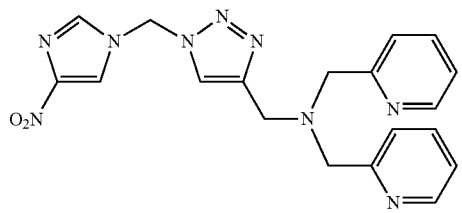

R1 = R3 = H
R1 = NO2
N = 1
R'1 = R'2 = H

Scheme 2

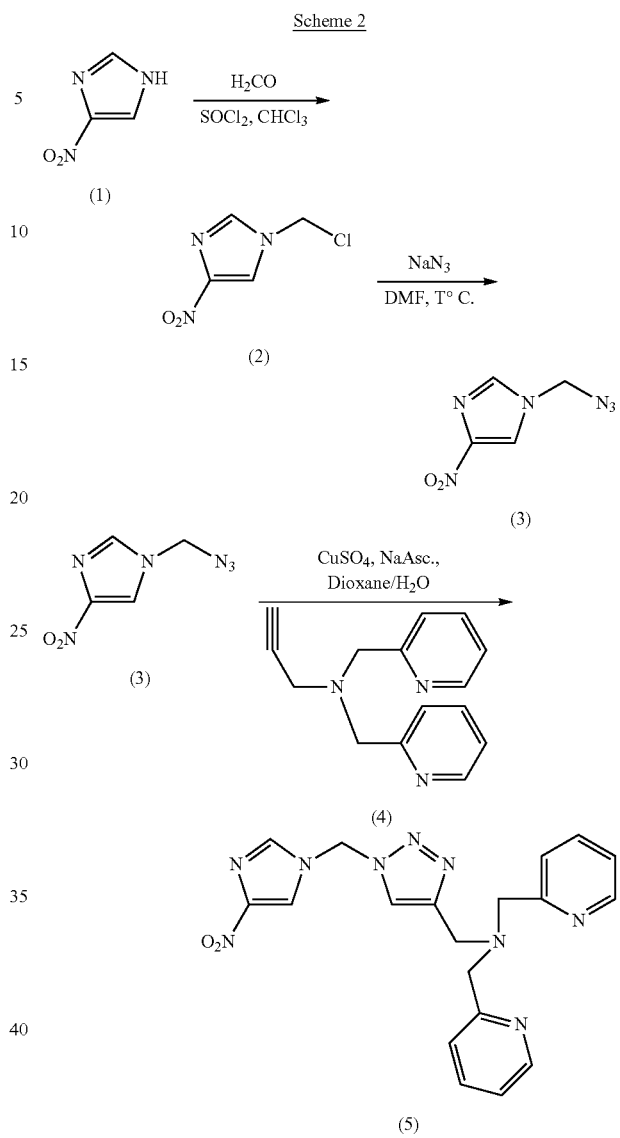

Typically 1-(Chloromethyl)-4-nitro-1H-Imidazole (2) was obtained by reacting 4-nitro-1H-Imidazole (1) with paraformaldehyde in the presence of thionyl chloride in chloroform. 1-(Azidomethyl)-4-nitro-1H-imidazole (3) was synthesized by reacting 1-(Chloromethyl)-4-nitro-1H-Imidazile (2) with sodium azide in DMF at 50° C. The reaction of di-(2-picolyl) amine with propargyl bromide in the presence of potassium carbonate in acetonitrile gave the propargyl di (2-picolyl) amine (4) in 87% yield "Click reactions with this compound and different arylazides (benzyl-, anthracenyl- or anthracenylmethylazide) gave the N,N'-bis (2-pyridylmethyl)-N"'-(4-triazolylmethyl)amino tripodal chelating system in 26-60% yield", A Click procedure with heterogeneous copper to tether technetium-99m chelating agents and rhenium complexes. Evaluation of the chelating properties and biodistribution of the new radiolabelled glucose conjugates. Eric Benoist, Yvon Coulais, Mehdi Almant, JoséKovensky, Vincent Moreau, David Lesur, Marine Artigau, Claude Picarda, Chantal Galaup, Sébastien G. Gouin. Carbohydrate Research, Volume 346, Issue 1, 2011, Pages 26-34, [7] and Eric Benoist et al., "A Click procedure with heterogeneous copper to tether technetium-99m chelating agents and rhenium complexes. Evaluation of the chelating properties and biodistribution of the new radiolabelled glucose conjugates", Carbohydrate Research, Volume 346, Issue 1, 3 Jan. 2011, Pages [26-34], [8] 4-nitro-1H-Imidazole-methyl-1,2,3-triazol-methyl-di-(2-pycolyl) amine (5) was obtained by the dissolution in a mixture of solvents dioxane/water at 100° C. of propargyl-di (2-picolyl) amine (4) with 1-(azidomethyl)-4-nitro-1H-imidazole (3) in the presence of copper sulphate, sodium ascorbate.

Ligand 4-nitro-1H-Imidazole-methyl-1,2,3-triazol-methyl-di-(2-pycolyl) amine (5) may also be purchased from HOLIS Technologies SA, Toulouse, France.

Example 2

Dendrimer

G10 and G5 polylysine dendrimers were purchased from the company Colcom, Cap Alpha, Clapiers, France.

These dendrimers are known for their safety in humans (VivaGel™ (SPL7013 Gel): A candidate dendrimer -microbicide for the prevention of HIV and HSV infection. Richard Rupp, Susan L Rosenthal, Lawrence R Stanberry and Richard Rupp, International Journal of Nanomedicine 2007:2(4) 561-566). [9]

In particular, the characteristics of fifth generation dendrimers are as follows: molecular weight 172300 g and estimated diameter 16 nm. This fifth-generation dendrimer has shown to be safe after intravascular injection either directly to the concentration of 100 mg/L. [H. BELHADJ-TAHAR et al., "Etudes de Toxicocinétique et de biodistribution de dendrimères de cinquième génération", 8èmes Journées Cancéropôle Grand Sud Ouest 10-12 Oct. 2012, MontpellierLett., 9 (2007), pp. 4999-5002]. [10]

Example 3

Mixture Dendrimer-Ligand

The ligand is mixed with the dendrimer in proportions of 1/1000, namely the ligand concentration was 4.8 millimoles/liter (4.8 mM/L) and the dendrimer concentration was 4.9 micromoles/liter (4, 9 µM/L).

The test items were stored at room temperature, away from light sources and humidity in a room especially designed to that effect. The product dissolved in sterile water was used within 2 hours after preparation.

Example 4

Complexation with a Transition Metal

A solution of dendrimer conjugate dosed at 0.087 mCi/µL (3.34 MBq/µL) was prepared by reacting 330 µL of a physiological solution of 1,725 mM 1-nitro-1H-Imidazole-methyl-1,2,3-triazol-methyl-di-(2-pycolyl)amine and 7.03 µM G5 dendrimer with radioactive carbonyltechnetium (28.86 mCi) and heated at 60° C. for 1 hour.

Experimental Protocols Common to Examples 5 and 6

Species: Wistar rats RjHan: Wi (free of specific pathogens)

Origin: Laboratoire JANVIER S.A.S, France. Animals delivered by the supplier were accompanied by a health assessment (to set acclimatization)

Number and sex and Weight: 6 healthy adult rats (males), average weight 300 g

Acclimatization: during 24 hours before the start of the test

Weight: D0, the day before the relevant step of the test, the animals were weighed.

The average weight is calculated and acceptable limits are deducted, extreme individual weights of animals should not be within ±20% of the average weight, ID: The animals are identified by a marking with indelible black felt on the coat (male rats numbered 1 to 6).

Accommodation: animals were housed at up to 3 per cage, in a 31 cm×46 cm×19 cm polypropylene cage fitted with a stainless steel cover. The cage was placed in a restricted access room, maintained under slight pressure (10 mm minimum water), under temperature-controlled atmosphere (T=22±2° C.) and controlled relative humidity (RH=50±20%) except during wash cycles and with an exchange of filtered fresh air (HEPA filter on) at 10 cycles per hour.

Bedding, regularly renewed, consisted of dust-free and γ rays sterilized sawdust.

Artificial lighting provided 12 hours of daylight and 12 hours of darkness.

Food: complete feed was supplied in pellet form A04-10

Drink: normal filtered water was distributed in polypropylene bottles fitted with a stainless steel nipple, a water sample was taken at least every six months and sent for physico-chemical and bacteriological analysis.

Example 5

Acute Toxicity Test and Biodistribution after Intravenous and Intraperitonial Administration in the Rat <<Dendrimer G5{1-Nitro-1H-Imidazole-Methyl-1,2,3-Triazol-Methyl-Di-(2-Pycolyl) Amine}>>

Test item:

Dendrimer G5 {1-nitro-1H-Imidazole-methyl-1,2,3-triazol-methyl-di-(2-pycolyl)amine}

Summary of the Test:

The aim of the study was to assess qualitatively and quantitatively the toxic effects and the delay of appearance after single administration of a pre-defined dose of 63, 4316 picomole/kg (33.17 mCi/kg or 1226 MBq/kg) of body weight, (corresponding to risk factor at 8 times of human equivalent dose), of test item diluted with distilled water by intravenous and intraperitoneal administration.

The experiment was conducted in two stages:

First step 3 groups of male rats:

Group 1 ("G5"): 2 rats (1 and 2) receiving 0.1 ml of labeled solution of dendrimer alone, one via intravenous administration, the other intraperitoneally 1

Group 2 ("G5-HLS"): 2 rats (3 and 4) receiving 0.1 ml of the solution of the test item "G5 dendrimer {1-nitro-1H-imidazole-methyl -1,2,3-triazol-methyl-di(2-pycolyl)amine}", one via intravenous administration, the other intraperitoneally Group 3 ("HLS"): 2 rats (n° 4 and 5) receiving 0.1 ml of the labeled 1-nitro-1H-imidazole-methyl -1,2,3-triazole-methyl-di-(2-pycolyl) amine, one via intravenous administration, the other intraperitoneally Second stage Rat No. 7: receiving 0.1 ml of labeled solution of dendrimer alone via intravenous administration Rat No. 8: receiving 0.1 ml of the solution of the test item "G5 dendrimer {1-nitro-1H-imidazole-methyl-1,2,3-triazol-methyl-di-(2-pycolyl)amine}" via intravenous administration Rat No. 9: 0.1 ml labeled solution of 1-nitro-1H-Imidazole-methyl-1,2,3-triazol-methyl-di-(2-pycolyl) amine via intravenous administration The animals were observed for 1 hour after administration and the signs of toxicity (mortality . . . ) were noted.

This test provided results allowing immediate innocuousness and tissular distribution verifying of the test item.

Labeled Sample with Dendrimer Alone

The labeled dendrimer solution dosed at 0.087 mCi/µL (3.34 MBq/µL) was prepared by reacting 330 µL of a G5 dendrimer physiological solution at 7.03 µM with radioactive carbonyltechnetium (28.86 mCi) and heated at 60° C. for 1 hour.

Labeled Sample of the Test Item

The solution of the test Item dosed at 0.087 mCi/µL (3.34 MBq/µL) was prepared by reacting 330 µL of a physiological solution of 1, 725 mM 1-nitro-1H-Imidazole-methyl-1,2,3-triazol-methyl-di-(2-pycolyl)amine and 7.03 µM G5 dendrimer with radioactive carbonyltechnetium (28.86 mCi) and heated at 60° C. for 1 hour.

Labeled Sample of 1-nitro-1H-Imidazole-methyl-1,2,3-triazol-methyl-di-(2-pycolyl) amine alone The solution of labeled 1-nitro-1H-Imidazole-methyl-1,2,3-triazol-methyl-di-(2-pycolyl)amine alone assayed at 0.087 mCi/µL (3.34 MBq/µL) was prepared by reacting 330 µL of 1.725 mM physiological solution of 1-nitro-1H-Imidazole-methyl-1,2,3-triazol-methyl-di-(2-pycolyl)amine with radioactive carbonyltechnetium (28.86 mCi) and heated at 60° C. for 1 hour.

Each sample was kept in a type I 15 mL sterile glass vial (type Elumatic International CisBio).

Results:

0% of mortality at the dose of 63,4316 picomole/kg (33.17 mCi/kg=1226 MBq/kg) (corresponding to risk factor at 8 times of human equivalent dose).

Conclusion:

The test item diluted with distilled water was verified for a dose at 63,4316 picomole/kg (33.17 mCi/kg=1.226 MBq/kg); (corresponding to risk factor at 8 times of human equivalent dose)

Example 6

Acute Toxicity Test and Biodistribution after In Situ Administration by Direct Intrahepatic Injection in the Rat <<Dendrimer G5{1-Nitro-1H-Imidazole-Methyl-1,2,3-Triazol-Methyl-Di-(2-Pycolyl)Amine}.

Test Item:

Dendrimer G5{1-nitro-1H-Imidazole-methyl-1,2,3-triazol-methyl-di-(2-pycolyl)amine}

Summary of the Test:

The aim of the study was to assess qualitatively and quantitatively the toxic effects and the delay of appearance after single in situ intrahepatic administration of pre-defined dose of 5.72 mCi/kg (209.969 MBq/kg of body weight, of test item diluted with distilled water.

The experiment was conducted as follows: 3 male rats:

Rat 1: receiving 0.1 ml of the labeled solution of dendrimer alone by direct hepatic injection into the 'right-hand' lobe after laparotomy under general anesthesia Rat 2: receiving 0.1 mL, of the solution of the test item G5 dendrimer {1-nitro-1H-Imidazole-methyl-1,2,3-triazol-methyl-di-(2-pycolyl) amine }by direct hepatic injection into the 'right-hand' lobe after laparotomy under general anesthesia Rat 3: receiving 0.1 nil of the labeled solution of 1-nitro-1H-Imidazole-methyl-1,2,3-triazol-methyl-di-(2-pycolyl) amine by direct hepatic injection into the 'right-hand' lobe after laparotomy under general anesthesia The animals were observed for 1 hour after administration and the signs of toxicity (mortality . . . ) were noted. Then, all animals were sacrificed and the biodistribution study was carried out.

Given the nature of the test item, the test began with one animal (step 1) receiving a dose of 33.17 mCi/kg (1226 MBq/kg) of test item. After this first step, according to the methodology and the recommendations of the OECD, the test was continued on other animals receiving the test item at a dose of 33.17 mCi/kg (1226 MBq/kg) of body weight, in the same conditions as the animals of step 1.

Administration of Test Item

The administration volume per kg of body weight has been initially set to 33.17 mCi/kg. The volumes of test item to administer were calculated for each rat. The concentration of the stock solution of the Test Item was 0.087 mCi/µL (3.34 MBq/µL).

The test item was administered once, by intravenous and intra péritoniale, using a suitable volume of syringe, fitted with a needle of suitable size.

Autopsy

All animals surviving to the end of 60 minutes of observation were euthanized at T=60 min by intraperitoneal injection of sodium Pentobarbital® 6% at a dose of 1.16 ml/kg and were bled at the femoral artery. They were autopsied and major organs were observed macroscopically. All pathological changes were recorded in a document reserved for this purpose.

Biodistribution

The removed organs (brain, kidney, liver, heart, intestine, lung, gonads, blood, urine) were weighed and their activities were counted on NaI gamma camera.

This test provided results allowing immediate innocuousness and tissular distribution verifying of the test item.

Pharmaceutical quality was ensured by the Pharmacy Usage Indoor (PUI) of PURPAN. It consisted in:

PH control

Control of the chemical purity of the solid product by gas chromatography (by BOLTS Technology)

Sterility control (a posteriori)

Control of pyrogens (a posteriori).

Results:

0% of mortality at the dose of 5.72 mCi/kg (209.969 MBq/kg) (corresponding to risk factor at 1,3 times of human equivalent dose). The hepatic binding rate of the test item is estimated at 53.7% corresponding to 33.5% of initial injected dose by hepatic mass charged with the test item, then the ratio of liver binding obtained through in situ/intravascular was calculated at 2190% (33.5% DIg/1.53% DIg).

Result interpretation:

The assessment criteria of the toxicity of the test item which were taken into account are:

Clinical and behavioral signs

Autopsy observations

Mortality expressed as the number of dead animals due to the test item.

The activity of the test item as a function of the animal body weight

Conclusion:

The test item diluted with distilled water was verified for a dose at 5.72 mCi/kg (209.969 MBq/kg (corresponding to risk factor at 1,3 times of human equivalent dose). The hepatic binding rate of test item is estimated at 53.7% corresponding to 33.5% of initial injected dose by liver mass charged with test item, then the ratio of in situ/intravascular rate was calculated at 2190%.

Pharmacologic properties

Results for Examples 5 and 6 are depicted in FIGS. 2 to 6.

It has been shown by the studies in male Wistar Rats, that the dendrimer conjugate according to the invention has no acute toxicity, even after direct injection at a concentration of 63.4316 pmol/kg (activity 33.17 mCi/kg or 1226 MBq/kg) (corresponding to a safety factor of 8 times the equivalent dose of the product administered to human beings) in the bloodstream intravenously. Similarly no precipitation was observed or thrombus formation at the injection site.

The therapeutic effect is based on the radiotoxic action of rhenium on cancer cells. This effect targets the cancer cells, that is why we talk about the concept of targeted therapy, and this for 3 effects of the dendrimer conjugate of the invention:

1. This is possible thanks to the ligand that preferentially accumulates in the cancer cells.
2. In situ administration of the dendrimer conjugate. Examples of modes of in situ administration of the dendrimer conjugate: (i) deposit of the dendrimer conjugate directly on the tumor via direct introduction, (ii) intra-arterial administration by means of interventional radiology.
3. The use of the dendrimer as supravecteur solution to accurately deposit the hot radio-element.

Furthermore, in situ administration in the male Winstar rat, which involves a laparotomy and direct injection into a liver segment, showed that the dendrimer conjugate remains almost stable at the site of introduction. Indeed, the in situ fixation rate of the test item is estimated to 2190% relative to the liver fixation obtained by intravascularly administration. The assessment of radioactivity was carried out on the various organs and the carcass alone, urine and whole blood.

Figure 6:
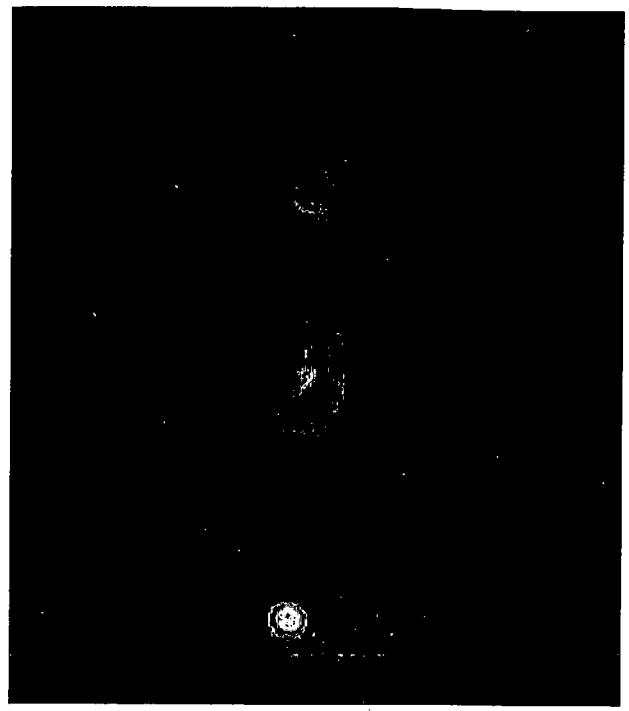
FIG. 6 represents a scintigraphic picture in rats after intra-arterial administration of the product, and animal sacrifice a few hours after administration. The injection was made at a hepatic lobe (very intense point on the photo). Organs were collected and separated and analyzed by the gamma camera. This picture validates the concept of targeted therapy of the dendrimer conjugates of the present invention: indeed, in situ product administered remains largely in its activity site (tissue biodistribution negligible after several hours).

FIG. 6 is a scintigraphic image of biodistribution after injection: it will be noted that only the liver, stomach and intestines are discernible. Note that we acquired 600 rounds/minute for 10 minutes for maximum sensitivity: the dendrimer conjugate has not moved a lot from the site of its deposition, and biodistribution reaches a maximum at the injection site.

Thus, it can be qualified as a targeted therapy because the radio-element biodistribution outside the targeted site is negligible.

This therapy allows to follow as the therapeutic agent (dendrimer conjugate) via diagnostic gamma camera: no need to add a radiopaque excipient to monitor administration, including with intra-arterial administered.

Example 7

Exemplary Pharmaceutical Product Form

Radionuclides:

We have 188Rhenium, 186Rhenium and radioactive trace level. Isotopes and 188Rhénium 186Rhenium are beta emitters of high energy (Eβ=777 key and Eβ=326.1 keV) and short half-life of 0.71 day and 3.78 day respectively.

Dose to be Injected:

1.3 GBq (35 mCi) dose that systemically induces no significant toxicity in humans.

[Dose escalation study with rhenium-188 hydroxyethylidene diphosphonate in prostate cancer patients with osseous metastases. Palmedo H, Guhlke S, Bender H, Sartor J, Schoeneich G, Risse J, Grünwald F, Knapp FF Jr, Biersack H J. Eur J Nucl Med. 2000 February; 27 (2):123-30]. [11]

Ligand Vector:

We have a tetradentate ligand with pattern 2-methyl-1-aminocyclopentène dithiocarboxylate coupled with imidazole. This tracer showed a high affinity and specificity for hypoxic cells.

[Conceptualization and assessment of original probes for hypoxic cell exploration. H. Belhadj-Tahar, Y. COULAIS and M. VIDAL. 2nd Symposium "Novel Targeting drugs and radiotherapy", 14-15 Jun. 2007, Toulouse (France)] [12]

Complexation Method:

The radiometal is complexed at high affinity sites (ligands). Attachment at these sites is kinetically more favorable than the site-specific recognition of the biomolecule (Imidazole) that targets hypoxic cells.

The Supravector

The dendrimer is used cyclotriphosphazene-phenoxymethyl (methylhydrazono) dendrimer, generation 1.5. This is a macromolecule of molecular weight: 2855.51 g/mol volume of distribution and therefore limits diffusion of localized at the tumor stroma.

* CAS 89939-12-6: Not dangerous substance classified as the (according to Directive 67/548/EEC)

Exemplary Final Manufactured Products Marketed

The Cold Kit Precursor in a Sealed Bottle:

The kit contains a lyophilized product comprising the vector polydentate di-aminothiol reduced affinity for the metal and also contains the reducing agent (tin chloride) and citric acid (participating in the buffer effect of the returned product extemporaneously).

a) Description Bottle A:

The lyophilisate ligand

Citric acid (pH adjustment)

Tin chloride b) Description Bottle B

Polylysine sterile lyophilized c) Preparation of Extemporaneous Bottle A:

Introduction of the sodium perrhenate in the flask A, to the flask in a shaker thermostated at 40° C.

d) Preparation of Extemporaneous Bottle B

Transfer the contents of vial A and B obtained in the bottle; incubate 1 hour at room temperature in a shaker sweet.

Preparation Before Administration, Administered Product.

The preparation is made from a

The cold kit precursor

From radiometal from saline and sterile freshly eluted generator Tungsten-Rhenium: the radiocontrols are performed on the eluate from the radiopharmacist.

The product to be delivered is inserted into the sealed vial.

Administration is maximum 4 h after preparation.

The administration is performed by the radiologist.

Figure 7:
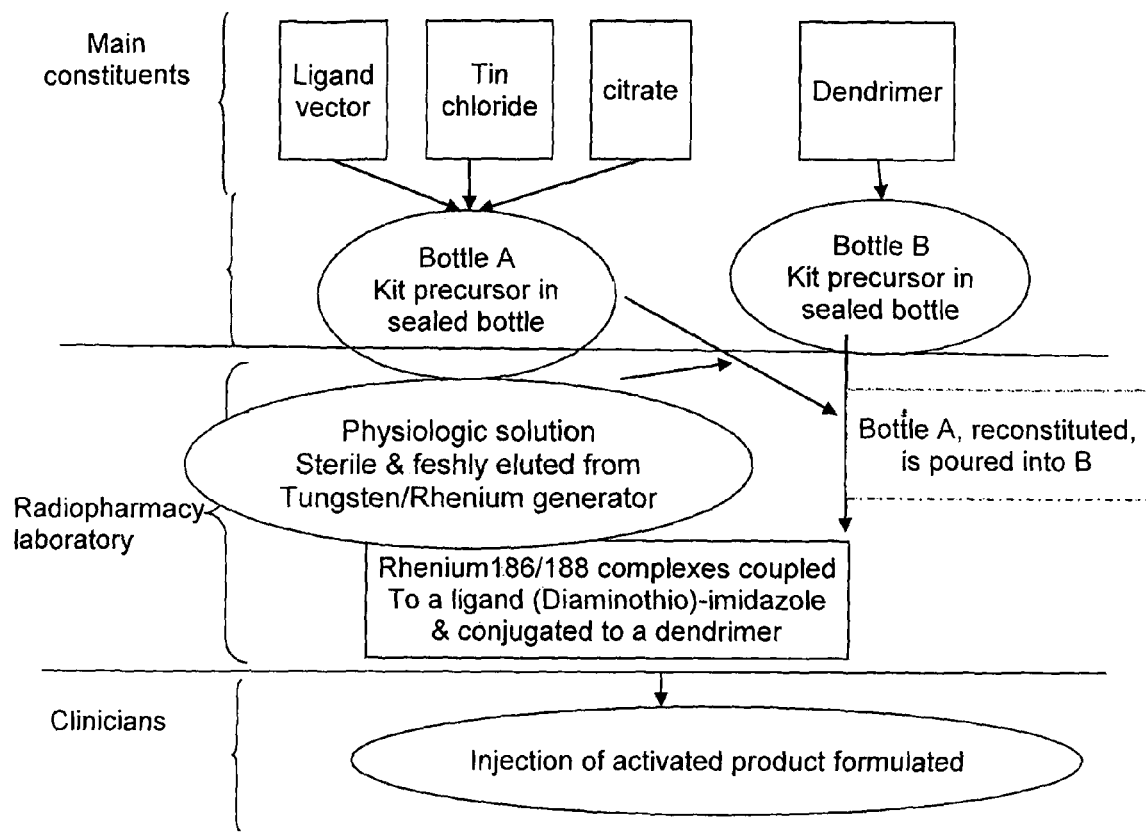
FIG. 7 represents a general scheme of the method of formulation and administration of a dendrimer conjugate according to the invention.

A general scheme of a method of formulation and administration of a dendrimer conjugate according to the present invention is illustrated in FIG. 7.

Route of Administration:

The route of administration is intra-arterial route, which is to say that the product is deposited in situ by the radiologist.

The presence of dendrimer will limit the tissue distribution of rhenium related to imidazole, unlike yttrium which is deposited in the form of beads and the presence of imidazole more will increase the transport rhenium bound to the cancer cell, in fact, the cancer process induces a hypoxic [13] and the imidazole derivatives are best captured by hypoxic cells and/or cancer.

Thus, the route of administration and intra-arterial drug design will greatly reduce tissue distribution of radioactive rhenium and will also greatly reduce the spread of the radioactive rhenium in normal cells.[14]

Frequency of Administration:

Given the half-life of rhenium which is a few days and given the experience of the radiologists with our clinicians Yttrium, treatment consists of a single injection of the drug preparation containing radioactive rhenium.

Example 8

Exemplary Pharmaceutical Product Form

Example 7 was repeated by using polylysine dendrimer G5 instead of cyclotriphosphazene-phenoxymethyl (methylhydrazono) dendrimer, generation 1.5; and 1-nitro-1H-Imidazole-methyl-1,2,3-triazol-methyl-di-(2-pycolyl)amine instead of tetradentate ligand with pattern 2-methyl-1-aminocyclopenténe dithiocarboxylate coupled with imidazole as ligand.

While we have described a number of embodiments of this invention, it is apparent that our basic examples may be altered to provide other embodiments that utilize the compounds and methods of this invention. Therefore, it will be appreciated that the scope of this invention is to be defined by the appended claims rather than by the specific embodiments that have been represented by way of example.

LIST OF REFERENCES

[1] Launay et al., Angew. Chem. Int. Ed. Engl., 1994, 33, 15/16, 1590-1592.
[2] Launay et al., Journal of Organometallic Chemistry, 1997, 529, 51-58.
[3] Adams G. Hypoxia-mediated drugs for radiation and chemotherapy. Cancer, 1981; 48; 696-707.
[4] Brizel D M et al. Tumour oxygenation predicts for the likelihood of distant metastases in human soft tissue sarcoma. Cancer Res. 1996; 56: 941-943.
[5] Seddon B M et al. The role of functional and molecular imaging in cancer drug discovery and development. Brit J Radial. 2003; 76: S128-S138.
[6] Salem R et al. Radioembolization for hepatocellular carcinoma using yttrium-90 microspheres: a comprehensive report of long-term outcomes. Gastroenteroly. 2010; 138(1): 52-64.
[7] Eric Benoist et al., "A Click procedure with heterogeneous copper to tether technetium-99m chelating agents and rhenium complexes. Evaluation of the chelating properties and biodistribution of the new radiolabelled glucose conjugates", Carbohydrate Research, Volume 346, Issue 1, 2011, Pages 26-34.
[8] Eric Benoist et al., "A Click procedure with heterogeneous copper to tether technetium-99m chelating agents and rhenium complexes. Evaluation of the chelating properties and biodistribution of the new radiolabelled glucose conjugates", Carbohydrate Research, Volume 346, Issue 1, 3 Jan. 2011, Pages 26-34.
[9] Richard Rupp et al., "A candidate dendrimer-microbicide for the prevention of HIV and HSV infection", International Journal of Nanomedicine 2007:2(4) 561-566.
[10] H. BELHADJ-TAHAR et al., "Etudes de Toxicocinétique et de biodistribution de dendrimères de cinquième génération", 8èmes Journées Canceropôle Grand Sud Ouest 10-12 Oct. 2012, MontpellierLett., 9 (2007), pp. 4999-5002.
[11] Palmedo H. et al., "Dose escalation study with rhenium-188 hydroxyethylidene diphosphonate in prostate cancer patients with osseous metastases", Eur J Nucl Med. 2000 February; 27 (2):123-30.
[12] H. Belhadj-Tahar et al., "Conceptualization and assessment of original probes for hypoxic cell exploration", 2nd Symposium "Novel Targeting drugs and radiotherapy", 14-15 Jun. 2007, Toulouse (France).
[13] Kunz M, Ibrahim M S. Molecular responses to hypoxia in tumor cells. Mol Cancer. 2003; 2: 1-13.
[14] Raleigh et al. Derivatives of 2-nitroimidazole as hypoxic cell markers. U.S. Pat. No. 5,674,693 du Jul. 10, 1997 et Siemens Medical, Nitro-imidazole hypoxia imaging agents. US Patent No US 2011/0002850 A1 du Jun. 1, 2011.
[15] U.S. Patent documents cited in this application:
[16] U.S. Pat. Nos. 4,507,466, 4,558,120 4,568,737, 4,587,329, 4,631,337, 4,694,064, 4,713,975, 4,737, 550, 4,857,599, 4,871,779, 5,338,532, 6,471,968, 5,387,617, 5,393,797 , 5,393,795, 5,527,524, 5,560,929 , 5,773,527, 5,631,329, 5,935,114; 5,908,413; 5,792, 105; 5,693,014; 5,674,192; 5,876,445; 5,913,894; 5,868,719; 5,851,228; 5,843,089; 5,800,519; 5,800, 508; 5,800,391; 5,354,308; 5,755,722; 5,733,303; 5,866,561; 5,857,998; 5,843,003; and 5,933,145.

The invention claimed is:

1. A dendrimer conjugate comprising a G2 to G10 polylysine dendrimer conjugated with a nitroimidazole ligand/metal complex having the following structure:

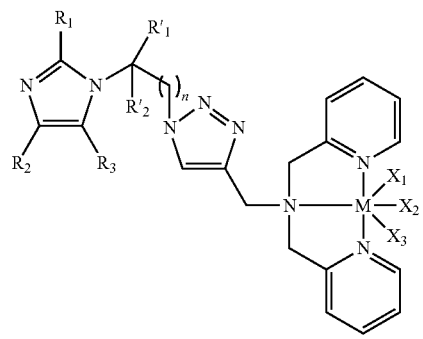

wherein n is an integer from 0 to 8 inclusive;

R1, R2 and R3 independently represent H, $NO_2$ or methyl;

R'1 and R'2 independently represent H, OH, methyl, ethyl or propyl;

X1, X2 and X3 independently are absent or represent, CO or $H_2O$ as allowed by the valence of metal M; and M represents a radioactive or non radioactive isotope of a transition metal selected from Y, Zr, Nb, Mo, Tc, Ru, Rh, Pd, Ag, Cd, Re, In or Sn, wherein said conjugation comprises ionic bonds, metallic bonds, hydrogen bonds or Van de Waal's bonds.

2. The dendrimer conjugate of claim 1, wherein the dendrimer has the following structure:

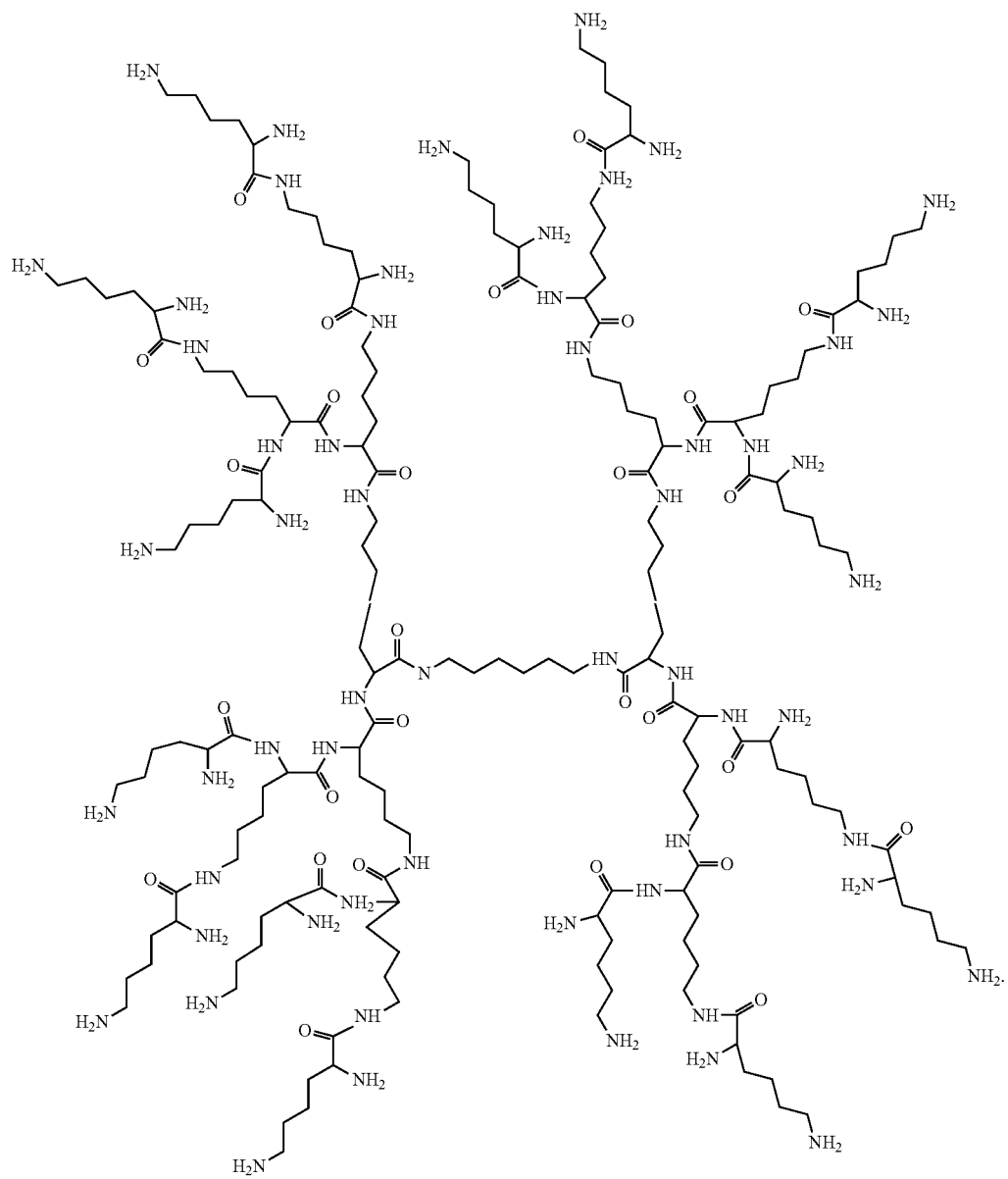 [SMILES: NCCCCC(N)C(=O)NCCCCC(N)C(=O)NCCCCC(NC(=O)C(CCCCNC(=O)C(N)CCCCN)NC(=O)C(N)CCCCN)C(=O)NCCCCC(NC(=O)C(CCCCNC(=O)C(CCCCNC(=O)C(N)CCCCN)NC(=O)C(N)CCCCN)NC(=O)C(CCCCNC(=O)C(N)CCCCN)NC(=O)C(N)CCCCN)C(=O)NCCCCCCNC(=O)C(CCCCNC(=O)C(CCCCNC(=O)C(CCCCNC(=O)C(N)CCCCN)NC(=O)C(N)CCCCN)NC(=O)C(CCCCNC(=O)C(N)CCCCN)NC(=O)C(N)CCCCN)NC(=O)C(CCCCNC(=O)C(CCCCNC(=O)C(N)CCCCN)NC(=O)C(N)CCCCN)NC(=O)C(N)CCCCNC(=O)C(N)CCCCN]
3. The dendrimer conjugate of claim 1, wherein the nitroimidazole ligand/metal complex has the following structure:
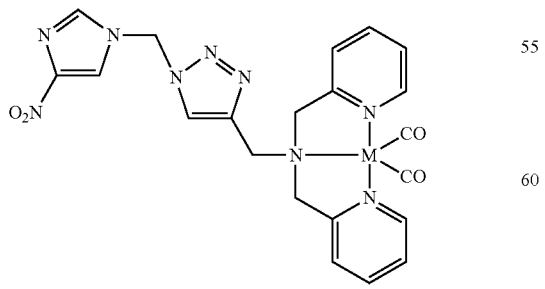
wherein M represents $^{99m}$Tc or $^{186/188}$Re.
4. The dendrimer conjugate of claim 1, wherein the conjugate has the following structure:

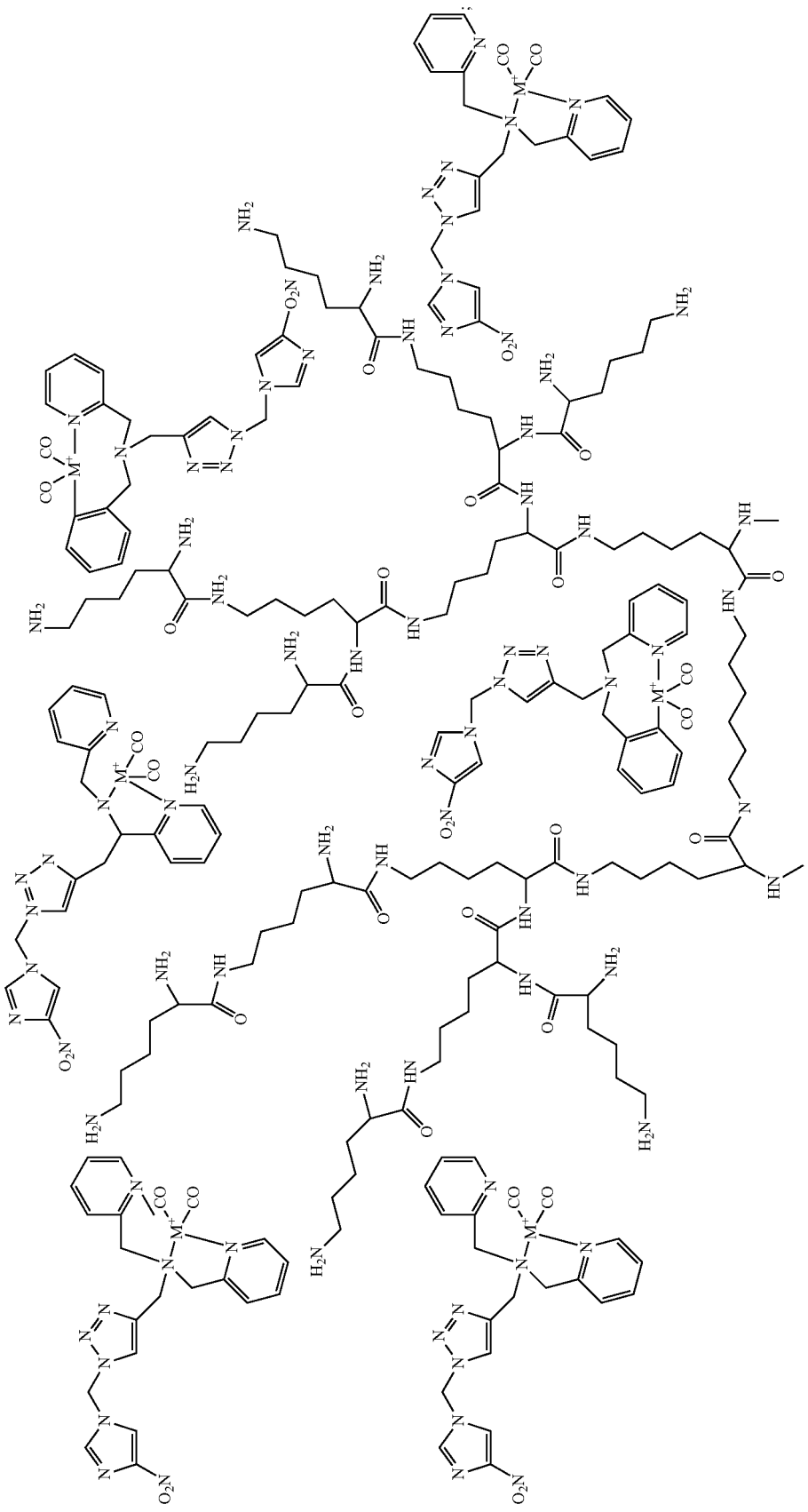

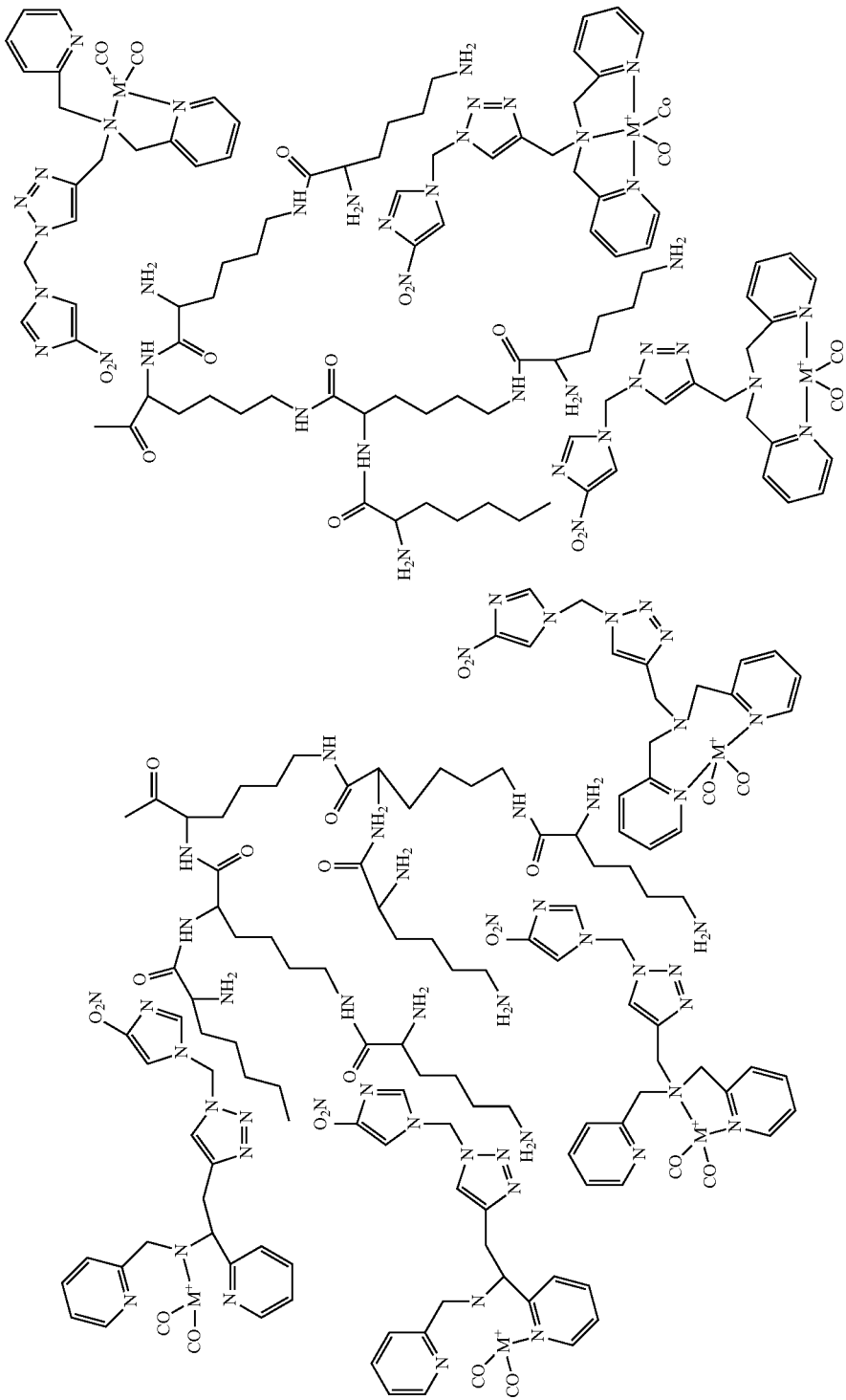

wherein M represents $^{99m}$Tc or $^{186/188}$Re.

5. A pharmaceutical composition comprising a dendrimer conjugate of claim 1 and a pharmaceutically acceptable carrier.

6. The composition of claim 5, wherein M is $^{186/188}$Re and the composition is a radiopharmaceutical composition.

7. The composition of claim 5, wherein M is $^{99m}$Tc and the composition is a diagnostic composition.

8. A method of treating or lessening the severity of cancer comprising administering to a subject suffering from or susceptible to said cancer a therapeutically effective amount of the composition of claim 5.

9. The method of claim 8, wherein said cancer is selected from the group consisting of, lymphoma, Hodgkin's disease, non-Hodgkin's disease, Multiple myeloma, Waldenstrom's macroglobulinemia, Heavy chain disease, solid tumors, sarcomas and carcinomas, fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, brain cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, uterine cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, and neuroblastomaretinoblastoma and all solid tumors.

10. The method of claim 8, wherein administering comprises injecting the composition intraarterially through interventional radiography, intratumorally or peritumorally, and all kind of administration achieving in situ deposition of the therapeutic agent.

11. The method of claim 8, wherein administering a therapeutically effective amount of the composition comprises administering a dose between about 37 MBq/kg of $^{188}$Re corresponding to 5,4 $10^{-12}$ mol metal/kg of the subject's body weight and about 68 MBq/kg of $^{188}$Re corresponding to 9,96 $10^{-12}$ mol metal/kg of the subject's body weight.

12. A method of altering tumor growth in a subject, comprising: a) providing a composition comprising a dendrimer conjugate according to claim 5 and b) administering to a subject in need thereof a therapeutically effective amount of said composition under conditions such that said tumor growth is altered.

13. The method of claim 12, wherein said altering comprises inhibiting tumor growth in said subject.

14. The method of claim 12, wherein said altering comprises reducing the size of said tumor in said subject.

15. The method of claim 12, wherein the tumor is a primary or metastatic tumor.

16. The method of claim 12, wherein said composition comprising a dendrimer conjugate is co-administered with a chemotherapeutic agent or anti-oncogenic agent.

17. The method of claim 16, wherein said chemotherapeutic agent is selected from the group consisting of platinum complex, verapamil, podophylltoxin, carboplatin, procarbazine, mechloroethamine, cyclophosphamide, camptothecin, ifosfamide, melphalan, chlorambucil, bisulfan, nitrosurea, adriamycin, dactinomycin, daunorubicin, doxorubicin, bleomycin, plicomycin, mitomycin, bleomycin, etoposide, tamoxifen, paclitaxel, taxol, transplatinum, 5-fluorouracil, vincristin, vinblastin, and methotrexate.

18. A method for lymphatic system imaging, comprising:
administering to a subject an image enhancing amount of a dendrimer conjugate of claim 1, wherein the metal M is $^{99m}$Tc; and detecting a difference in an image signal intensity of at least a portion of the lymphatic system after the dendrimer conjugate is administered, wherein the difference in image signal intensity indicates the presence of metastatic cancer cells.

19. The method of claim 18, wherein the portion of the lymphatic system comprises a lymph node.

20. The method of claim 18, wherein administering comprises injecting the composition intravenously or intralymphatically.

21. The method of claim 18, wherein administering an imaging enhancing amount of the dendrimer conjugate comprises administering a dose between about 10.5 MBq of $^{99m}$Tc corresponding to 0.6 $10^{-12}$ mol metal/kg of the subject's body weight and about 26.3 MBq of $^{99m}$Tc corresponding to 1.5 $10^{-12}$ mol metal/kg of the subject's body weight.

* * * * *